(12) United States Patent
Yun et al.

(10) Patent No.: US 8,788,041 B2
(45) Date of Patent: *Jul. 22, 2014

(54) METHODS AND COMPOSITIONS FOR TREATING A DISEASE CONDITION IN A SUBJECT

(75) Inventors: Anthony Joonkyoo Yun, Palo Alto, CA (US); Patrick Yuarn-Bor Lee, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 928 days.

This patent is subject to a terminal disclaimer.

(21) Appl. No.: 12/886,327

(22) Filed: Sep. 20, 2010

(65) Prior Publication Data

US 2011/0029030 A1 Feb. 3, 2011

Related U.S. Application Data

(63) Continuation of application No. 11/251,629, filed on Oct. 14, 2005.

(60) Provisional application No. 60/619,158, filed on Oct. 15, 2004, provisional application No. 60/630,969, filed on Nov. 24, 2004, provisional application No. 60/650,192, filed on Feb. 3, 2005.

(51) Int. Cl.
*A61N 1/05* (2006.01)
*A61N 1/18* (2006.01)
*A61N 1/36* (2006.01)

(52) U.S. Cl.
CPC ............... *A61N 1/36117* (2013.01); *A61N 1/05* (2013.01); *A61N 1/18* (2013.01)
USPC .................... 607/44; 607/2; 607/40

(58) Field of Classification Search
CPC ........ A61N 1/36117; A61N 1/05; A61N 1/18
USPC .......................................................... 607/44
See application file for complete search history.

(56) References Cited

U.S. PATENT DOCUMENTS

| 5,707,400 | A | * | 1/1998 | Terry et al. ..................... 607/44 |
| 6,736,972 | B1 | | 5/2004 | Matson |
| 7,232,435 | B2 | | 6/2007 | Hildebrand et al. |
| 2003/0003165 | A1 | | 1/2003 | Hong et al. |
| 2005/0153885 | A1 | | 7/2005 | Yun et al. |
| 2005/0240241 | A1 | | 10/2005 | Yun et al. |
| 2006/0206149 | A1 | | 9/2006 | Yun |

FOREIGN PATENT DOCUMENTS

| WO | 0197797 | 12/2001 |
| WO | 2005034871 | 4/2005 |
| WO | 2005035731 | 4/2005 |

OTHER PUBLICATIONS

Goodman and Gilman's The Pharmacological Basis of Therapeutics, 10th Edition, Chapter 10 Catecholamines, Sympathomimetic Drugs and Adrenergic Receptor Antagonists, p. 233, published by The McGraw-Hili Companies in 2001.
Cameron etal., Psychosomatic Medicine 52:411-424,1990.
Gothoskar et al., Drug Delivery Technology, 4(5): Jun. 5, 2004.
A PDF regarding Compensatory Mechanism in Heart Failure, Pharmacotherapy, 20(9), 2000.

* cited by examiner

*Primary Examiner* — Bong-Sook Baek
(74) *Attorney, Agent, or Firm* — Bozicevic, Field & Francis LLP; Bret E. Field

(57) ABSTRACT

Methods for treating a disease condition in a subject are provided. The subject methods are characterizing by enhancing at least one symptom of the disease condition in a manner effective to cause the subject to mount a compensatory response effective to treat the disease condition. Also provided are compositions, kits and systems for practicing the subject methods.

8 Claims, 1 Drawing Sheet

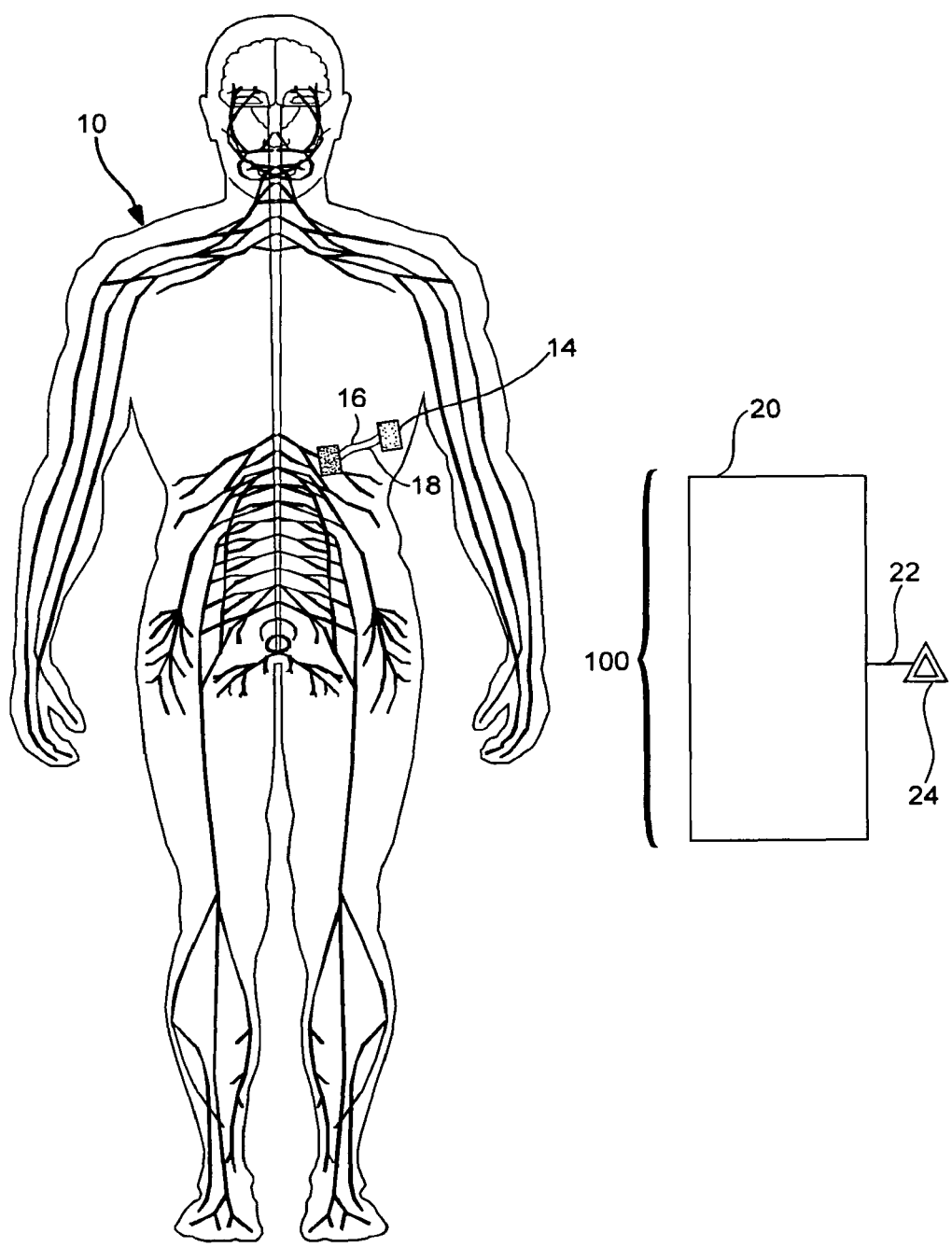

METHODS AND COMPOSITIONS FOR TREATING A DISEASE CONDITION IN A SUBJECT

CROSS-REFERENCE TO RELATED APPLICATIONS

Pursuant to 35 U.S.C. §119 (e), this application claims priority to the filing date of: U.S. Provisional Patent Application Ser. No. 60/650,192 filed on Feb. 3, 2005; U.S. Provisional Patent Application Ser. No. 60/630,969 filed on Nov. 24, 2004; and U.S. Provisional Patent Application Ser. No. 60/619,158 filed on Oct. 15, 2004; the disclosures of which applications are herein incorporated by reference.

INTRODUCTION

Background of the Invention

Reversing chronic conditions remains an elusive goal of medicine. The modern medical paradigm based on blocking or promoting abnormal pathways offers symptomatic benefit, but tolerance to therapy can develop and treatment cessation can produce rebound symptoms and tachyphylaxis due to compensatory mechanisms. Tolerance is defined as either a situation requiring dose escalation to maintain the therapeutic effect or a decreasing response to the repeat similar dosing. A classic example is the use of beta-blockers for hypertension, in which abnormally-high sympathovagal ratio represents one of the therapeutic targets. With time, chronic sympathetic blockade with beta-blockers may induce compensatory elevation of sympathovagal ratio, thereby creating higher dosing requirements and the potential for rebound hypertension upon cessation.

SUMMARY OF THE INVENTION

Methods for treating a disease condition in a subject are provided. The subject methods include enhancing at least one symptom of the disease condition to be treated in a manner effective to cause the subject to mount a compensatory response effective to treat the disease condition. Also provided are compositions, kits and systems for practicing the subject methods.

BRIEF DESCRIPTIONS OF THE DRAWINGS

FIG. 1 shows an exemplary embodiment of an electric energy applying device operatively positioned in a subject's body in accordance with embodiments of the subject methods.

DESCRIPTION OF THE REPRESENTATIVE EMBODIMENTS

Methods for treating a disease condition in a subject are provided. The subject methods include enhancing at least one symptom of the disease condition in a manner effective to cause the subject to mount a compensatory response effective to treat the disease condition. Also provided are compositions, kits and systems for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Overview

Aspects of the invention include methods of treating a subject for a disease condition. In the subject methods, at least one symptom of the disease condition is enhanced in a manner effective to cause the subject to mount a compensatory response effective to treat the disease condition. By "enhanced" is meant that the magnitude of the symptom is increased. In other words, the target symptom or symptoms is exacerbated. In certain embodiments, the magnitude of enhancement is at least about two-fold, e.g., at least about 5-fold, or more. The term "symptom" is used broadly to refer to any characteristic or sign of the disease condition, i.e., parameter, where symptoms may be any of a number of different types of parameters, including, but not limited to: sympathovagal ratio, high blood pressure, shortness of breath, variations from normal of one or more blood analytes, depression, sleeplessness, and the like. Representative parameters of interest and ranges that can be employed as reference values are provided in Table 1, below:

TABLE 1

| Parameter | Test | Normal Range of Values | Range of Interest |
|---|---|---|---|
| pulmonary gas | Alveolar oxygen | 650-713 mmHg | 600-713 mmHg |
| serum blood gas | pH | 7.35-7.45 | 7.1 to 7.7 |
|  | arterial pO2 | 80-100 mmHg | 50-110 |
|  | arterial pcO2 | 35-45 mmHg | 10 to 80 |
|  | arterial bicarb | 25-35 meq/L | 10 to 40 |
|  | alveolar/oxygen ratio | 0.8 | 1 to 0.6 |
|  | aa gradient | 10-15 mmHg | 5 to 120 |
|  | venous oxygen sat | 60% | 30-80% |
| cardoipulmonary | cardiac output | 3.5 to 5.5 L/min | 1 to 6 |
|  | cardiac index | 2.8-3.2 L/min/m2 | 0.5 to 6 |
|  | right atrial pressure | 1-7 mmHg | 1 to 30 |
|  | right ventricular systolic pressure | 15-25 mmHg | 5 to 50 |
|  | right ventricular diastolic pressure | 0-8 mmHg | 1 to 50 |
|  | pulmonary arterial systolic pressure | 15-25 mmHg | 5 to 50 |
|  | pulmonary arterial diastolic pressure | 8-15 mmHg | 1 to 30 |
|  | mean pulmonary arterial pressure | 10-20 mmHg | 5 to 50 |
|  | pulmonary capillary wedge pressure | 6-12 mmHg | 1 to 20 |
| pulmonary function test | tidal volume | 8-15 ml/Kg | 2-20 or 20-80% |
|  | total lung capacity | 5-7 liters | 3 to 10 or 20-120% |
|  | residual volume | 1.5 to 2.5 liters | 0.5 5 or 20-120% |
|  | forced expiratory volume in 1 second | 3.5-4 liters | 0.5 to 6 or 20-120% |
|  | functional vital capacity | 4-6 liters | 0.5 to 6 or 20-120% |
|  | FEV1/FVC ratio | >75% | 20-120% |
|  | forced expiratory flow | 75-125% | 50 to 150% |
|  | peak expiratory flow rate | 80-100% | 60-120% |
|  | forced expiratory time | <5 seconds | 0-20 seconds |
|  | corrected diffusion capacity | 75-80% | 60-140% |
|  | corrected QT interval | <440 | <600 |
| sleep study | sleep latency | >10 min | 0-1 hour |
|  | total sleep time | >5.5 hours | 0-12 hours |
|  | percent rem | >15% of TST | 0-40% total sleep time |
|  | percent stage 3-4 non rem | >25% of TST | 0-50% total sleep time |
|  | respiratory arousal index | <5/hour total sleep time | 0-40/hour total sleep time |
|  | periodic leg movements | <1/hour total sleep time | 0-40/hour total sleep time |
|  | apnea index | <1/hour total sleep time | 0-20/hour total sleep time |
|  | hypopnea index | <3/hour total sleep time | 0-40/hour total sleep time |
|  | nadir oxygen saturatin | >92% | 40-100% |
|  | mean oxygen saturation | >95% | 40-100% |
|  | desaturation index | <5 defined as >4% for 5 seconds/hour of total sleep time | 0-40 defined as >4% for 5 seconds/hour of total sleep time |
|  | highest carbon dioxide | 52 mmHg | 10-80 mmHg |
|  | carbon dioxide >45 mmHg | <20% of total sleep time | 0-60% of total sleep time |
| Serum Markers | Catecholamine levels |  |  |
|  | Acetycholine levels | 650-1500 IU/L | 300-2000 IU/L |
|  | Aldosterone levels | 17-70 nmol/day | 5-150 nmol/L/day |
|  | Renin levels | 7-76 uU/mL | 3-200 uU/ml |
|  | Vasopressin levels | 2-8 pg/mL | 1-20 pg/ml |
|  | angiotensin converting enzyme levels | 25-100 IU/L | 5-200 U/L |
|  | interleukin 1-3 and 5-13 and 18 | modulate |  |

TABLE 1-continued

| Parameter | Test | Normal Range of Values | Range of Interest |
|---|---|---|---|
| | Interleukin 4 | decrease | |
| | interferon alpha and beta | modulate | |
| | interferon gamma | increase | |
| | tumor necrosis factor alpha | modulate | |
| | transforming growth factor | modulate | |
| | hemoglobin A1C | 4-8% | 2-12% |
| | Fasting glucose | 3.5-6.0 mmol/L | 1-10 mmol/L |
| | high density lipoprotein | 45-60 | 10 to 90 |
| | low density lipoprotein | 95-130 | 60-200 |
| | triglyceride | <2 mmol/L | 4 to 4 mmol/L |
| | beta natriuretic peptide | 20-40 pg/mL | 0-100 pg/mL |
| | alpha natriuretic peptide | 20-40 pg/mL | 0-50 pg/mL |
| | erythrocyte sedimentation rate | 0-35 mm/Hour | 1-200 mm/Hour |
| | c reactive peptide | <10 mg/L | 1-80 mg/L |
| | transferrin | 1.75 to 3.13 g/L | 0.5 to 6 g/L |
| | Hemloglobin | 135-160 gm/L | 25 to 300 gm/L |
| | hematocrit | 37-54% | 25-60% |
| | ferritin | 20-240 ug/L | 5 to 600 ug/L |
| | iron | 10-40 umol/L | 5 to 100 umol/L |
| | cholinesterase | 650-1500 IU/L | 200-2500 IU/L |
| | Urine adrenaline | 0-80 nmol/day | 0-200 nmol/day |
| | Urine noradrenaline | 0-780 nmol/day | 0-1600 nmol/day |
| | Urine dopamine | 0-3500 nmol/day | 0-7000 nmol/day |
| | adrenocorticotrophic hormone | <19 pmol/L | 0 to 40 pmol/L |
| | antidiuretic hormone | 2-8 pg/mL | 1-20 pg/mL |
| | thrombin clotting time | 10-20 secs | 5-30 secs |
| | total serum cholesterole | 110-120 | 100-300 |
| Additional | body mass index | 20-30 | <40 |
| | systolic blood pressure | <125 | 90-180 |
| | diastolic blood pressure | <75 | 30-100 |
| | pulse pressure | <20 | 20-40 |
| | heart rate | 60-100 | 30-200 |
| | heart rate variability | increase | |
| | respiratory sinus arrhythmia | increase | |

In practicing the subject methods, the target symptom(s) is enhanced by applying an appropriate stimulus to the subject, where the stimulus is of a nature and magnitude sufficient to achieve the desired enhancement. In certain embodiments, the applied stimulus is one of short duration, where by short duration is meant that the applied stimulus lasts for less than about 1 week, e.g., less than about 3 days, e.g., less than about 1 day, e.g., less than about 12 hours, where the duration of the applied stimulus may be even shorter. Where the stimulus is a pharmacological stimulus, the duration refers to the period in which the pharmacological agent from an administered dosage is active. Where the stimulus is an electrical stimulus, the duration refers to the total of electrical applications received by a subject over a given period, analogous to a dose of a pharmacological agent.

Following symptom enhancement via an applied stimulus, as described above, the stimulus is removed, e.g., by metabolization of the pharmacological agent or cessation of application of electrical energy, and the subject is permitted to mount a compensatory response. In this following period, no additional stimulus is administered to the subject. The duration of this period between stimulus application, which may be referred to as a "holiday" period, may vary, but in representative embodiments is at least about 1 day, such as at least about 2 days, including at least about 5 days, at least about 10 days, at least about 15 days, or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied stimulus may vary, where in representative embodiments the stimulus may be a pharmacological stimulus and/or an electrical stimulus. As such, in certain embodiments, the stimulus is a pharmacological stimulus. In other representative embodiments, the stimulus is an electrical stimulus. In yet other embodiments, the stimulus is a combination of pharmacological and electrical stimuli. Accordingly, in certain embodiments, the enhancing is by administering a pharmacological agent to the subject. In yet other embodiments, the enhancing is by electrical stimulation, e.g., by employing an implanted electrical energy application device.

A variety of different disease conditions are treatable by the subject methods. In certain embodiments, the disease condition is one in which the body mounts a compensatory response to a stimulus administered to suppress or decrease one or more symptoms of the disease. In other words, the disease condition is one that is characterized by the presence of a compensatory response to a stimulus that reduces the magnitude of one or more symptoms of the disease. In certain embodiments, the disease condition is a condition that is characterized by the presence of a compensatory mechanism to a directly acting therapeutic approach.

In certain embodiments, the disease condition is a manifestation of an irregularity in a homeostatic pathway. In certain embodiments, the disease condition is manifested by chronic sympathetic bias. In certain embodiments, the pharmacological agent is adrenergic agonist, where the agent enhances the sympathetic bias in the short term, thereby causing the body to mount a compensatory mechanism. In certain embodiments, the stimulus is application of electrical energy that stimulates a sympathetic nerve(s) in a manner that enhances the sympathetic bias in the short term, thereby causing the body to mount a compensatory mechanism.

In certain embodiments, the disease condition is a cardiovascular disease. For example, short-term administration of adrenergic agonists may be employed in the treatment of hypertension, e.g., to achieve the desired short term increase or enhancement of sympathetic bias and concomitant long term decrease in sympathetic bias. In certain embodiments, the disease condition is a neurological condition. For example, short-term administration of a serotonin antagonist may be employed to treat depression, by causing a long-term compensatory response in the body in the form of increased serotonin receptor sensitivity. In certain embodiments, the disease condition is an immune condition. For example, a proinflammatory agent may be administered in short duration to treat asthma, where the short duration of proinflammatory agent cause the body to mount a compensatory response that results in decreased inflammation. In certain embodiments, the disease condition is an endocrine system condition. For example, in the treatment of diabetes, an insulin blocker may be administered on a short term basis, causing the body to mount a compensatory response, e.g., in the form of increased insulin receptor sensitivity. See the experimental section below for further discussion of these representative embodiments. In certain embodiments, the disease is not a pulmonary airway disease, e.g., asthma, emphysema or chronic obstructive pulmonary disease.

If a pharmacological approach is employed in the treatment of a given disease, the specific nature and dosing schedule of the agent will vary depending on the particular nature of the disease to be treated. Representative pharmacological agents that may find use in certain embodiments of the subject invention include both pro parasympathetic and pro sympathetic agents.

Pro parasympathetic agents of interest include, but are not limited to: Beta Blockers, e.g., atenolol (Tenormin R), betaxolol (Kerlone R), bisoprolol (Zebeta R), carvedilol (Coreg R), esmolol (Brevibloc R), labetalol (Normodyne R), metoprolol (Lopressor R), nadolol (Corgard R), pindolol (Visken R), propranolol (Inderal R), sotalol (Betapace R), timolol (Blocadren R); Aldosterone Antagonists, e.g., Spironolactone, eplerenone, Angiotensin II Receptor Blockade, candesartan (Atacand R), irbesartan (Avapro R), losartan (Cozaar R), telmisartan (Micardis R) valsartan (Diovan R), eprosartan mesylate (Teveten); ACE inhibitors, e.g., Benazepril (Lotensin R), Captopril (Capoten R), Enalapril (Vasotec R), Fosinopril (Monopril R), Lisinopril (Prinivil R), Moexipril (Univasc R), Quinapril (Accupril R), Ramipril (Altace R), Trandolapril (Mavik R); Statins, e.g., atorvastatin (Lipitor R), cerivastatin (Baycol R), fluvastatin (Lescol R), lovastatin (Mevacor R), pravastatin (Pravachol R), mvastatin (Zocor R); Triglyceride Lowering Agents, e.g., fenofibrate (Tricor R), gemfibrozil (Lopid R), Niacin; Diabetes Agents, e.g., acarbose (Precose R), glimepiride (Amaryl R), glyburide (Micronase R, Diabeta R), metformin (Glucophage R), Miglitol (Glycet R), pioglitazone (Actos R), repaglinide (Prandin R), rosiglitazone (Avandia R); Immunomodulators, e.g., Interferon Alfa-2A (Roferon-A), Interferon Alfa-2b (Intron-A), Interferon Alfa-2b and Ribavirin combo Pack (Rebetron), Interferon Alfa-N3 (Alferon N), Interferon Beta-1A (Avonex), Interferon Beta-1B (Betaseron), Interferon Gamma; agents that binds/reacts to CD4, gp39, B7, CD19, CD20, CD22, CD401, CD40, CD40L and CD23 antigens, rituximab, Nicotine; Sympathomimetics, e.g., trimethaphan, Clonidine, Reserpine, Guanethidine; Antihistamines, e.g., Benadryl, Diphenhydramine, Actifed (Triprolidine), PBZ (Tripelenamine), Allegra (Fexofenadine), Periactin (Cyproheptadine), Antivert or Bonine (Meclizine), Phenergan (Promethazine), Astelin (dispensed as a Nose Spray), Polyhistine (Phenyltoloxamine), Atarax (Hydroxyzine), Seldane (Terfenadine), Benadryl (Diphenhydramine), Semprex (Acrivastine), Bromfed (Brompheneramine), Tavist (Clemastine), Chlortrimeton (Chlorpheniramine), unisom (Doxylamine), Claritin (Loratidine), Zyrtec (Cetirizine), Dramamine (Dimenhydrinate); Cholinergics, e.g., Bethanechol, Oxotremorine, Methacholine, Cevimeline, Carbachol, Galantamine, Arecoline, Levaminsole; Acetylcholinesterase Inhibitors, e.g., Edrophonium, Neostigmine, Donepezil, Tacrine, Echothiophate, Diisopropylfluorophosphate, Demecarium, Pralidoxime, Galanthamine, Tetraethyl pyrophosphate, Parathoin, Malathion, Isofluorophate, Metrifonate, Physostigmine, Rivastigmine, Abenonium, acetylchol, Carbaryl acetylchol, Propoxur acetylchol, Aldicarb acetylchol, Muscarinics, Muscarine, Pilocarpine, Magnesium; Calcium channel blockers, e.g., amlodipine besylate, Norvasc, diltiazem hydrochloride Cardizem CD, Cardizem SR, Dilacor XR, Tiazac, felodipine Plendil, isradipine DynaCirc, DynaCirc CR, nicardipine Cardene SR, nifedipine Adalat CC, Procardia XL, nisoldipine Sular, verapamil hydrochloride Calan SR, Covera HS, Isoptin SR, Verelan; Sodium channel blockers, e.g., moricizine, propafenone, encamide, flecamide, Tocainide, mexiletine, Phenyloin, Lidocaine, Diisopyramide, Quinidine, Procainamide; Glucocorticoid receptor blocker, e.g., (Mifepristone); Peripheral adrenergic inhibitors, e.g., guanadrel Hylorel, guanethidine, monosulfate Ismelin, reserpine Serpasil, Mecamylamine, Hexamethonium; Blood vessel dilators, e.g., hydralazine hydrochloride Apresoline, minoxidil Loniten; Central agonists, e.g., alpha methyldopa Aldomet, clonidine hydrochloride Catapres, guanabenz, acetate Wytensin, guanfacine hydrochloride Tenex; Combined alpha and beta blockers, e.g., labetalol hydrochloride, Normodyne, Trandate, carvedilol Coreg; Alpha blockers, e.g., doxazocin mesylate Cardura, prazosin hydrochloride Minipress, terazosin, hydrochloride Hytrin; Combination diuretics, e.g., amiloride hydrochloride+hydrochlorothiazide Moduretic, spironolactone+hydrochlorothiazide Aldactazide, triamteren+hydrochlorothiazide Dyazide, Maxzide; Potassium-sparing diuretics, e.g., amiloride hydrochloride Midamar, spironolactone Aldactone, triamteren Dyrenium; Nitrate pathway modulators, e.g., L-arginine, Nitroglycerin Deponit, Minitran, Nitropar, Nitrocine, Nitro Disc, Nitro-Dur, Nitrogard, Nitroglycerin, Nitroglycerin T/R, Nitro-Time, Nitrol ointment, Nitrolingual Spray, Nitrong, Nitro-Bid, Nitropress, Nitroprex, Nitro S.A., Nitrospan, Nitrostat, Nitro-Trans System, Nitro-Transdermal, Nitro-Time, Transderm-Nitro, Tridil. Pentaerythrito, I Tetranitrate, Peritrate, Peritrate S.A, Erythrityl, Tetranitrate, Cardilate, Isosorbide Dinitrate/Phenobarbital Isordil w/PB Isosorbide, Mononitrate, Imdur, ISMO, Isosorbide, Mononitrate, Monoket, Isosorbide, Nitrate; Cyclic nucleotide monophosphodiesterase (PDE) inhibitors; e.g., Levitra (vardenafil), Cialis (tadalafil), Viagra (sildenafil); Vasopressin inhibitors, e.g., atosiban, Alcohol, Relaxin; Renin inhibitors; e.g., Aliskiren; Estrogen and estrogen analogues and estrogen metabolites; Vesicular monoamine transport (VMAT) inhibitors; e.g., reserpine, tetrabenazine, Melatonin, Melatonin Analogues, 6-chloromelatonin, 2,3, dihydromelatonin, 6-chloro-2,3-dihydromelatonin, N-acetyl-N-2-formyl-5-methoxy, kynurenamine, N-acetyl-5-methoxy kynurenamine; Progesterone inhibitors, e.g., ru486; Testosterone inhibitors, e.g., Spironolactone, cyproterone acetate; Gonadotropin-releasing hormone inhibitors, e.g., Leuprolide Acetate; Oxytocin inhibitors, e.g., Terbutaline Ritodrine, Glucagon Like Peptide 1; Dipeptidyl Peptidase IV inhibitors, e.g., LAF237 (novartis), P93/01 and P32/98 (Probiodrug AB), valine pyrrolidide (Novo Nordisk), dhea, adiponectin, phenserine, phosphodiesterase 4 inhibitor, valproate; Anticoagulants, e.g., Exanta (ximelagatran)—, Bilivarudin (hirulog), abciximab (Reopro®), Aggrenox® (dipridamole/ASA), anagrelide (Agrylin®), clopidogrel (Plavix), dipyridamole (Persantine®), tifabatide (Integrelin), ticlopidine (Ticlid®), tirofiban (aggrastat), ardeparin (Normiflo), Dalteparin (Fragmin), Danaparoid (Orgaran), Enoxaparin (lovenox), lepirudin (Refludan), Heparin, Warfarin; Thrombolytics, e.g., alteplase (Activase®, t-PA), reteplase (Retevase), Streptokinase, Urokinase; Other anticoagulants, e.g., aminocaproic acid (Amicar®), cilostazol (Pletal), erythropoietin (Epogen), filgrastim (G-CSF, Neupogen®), oprelvekin (Neumega), pentoxifylline (Trental); hmg1 antagonist; botox; and the like.

Pro sympathetic agents of interest include, but are not limited to: Beta-agonists, e.g., dobutamine, terbutaline, ritodrine, albuterol, metaproterenol; Alpha-1 agonists, e.g., phenylephrine, metaraminol, methoxamine; Prednisone & steroids; Indirect agents that include, but are not limited to, NE, ephedrine, phenylpropanolamine, cyclopentamine, tuaminoheptane, naphazoline, amphetamine, tetrahydrozoline; Epinephrine/norepinephrine, Acetylcholine, Sodium, Calcium, ACE, Angiotensin, Aldosterone, Aldosterone Analogues, Fludrocortisone, 18-oxocortisol, deoxycorticosterone pivalate (DOCP) (ciba-geigy animal health); Potassium or magnesium channel blockers, e.g., valproate lithium, Cocaine; Amphetamines, e.g., Ephedrine, Terbutaline, Dopamine, Bromocriptine (Parlodel), Levodopa/Carbidopa, Dobutamine; Acupuncture; Adh vasopressin; Oxytocin pitocin; THC cannabinoids; Progesterone; Leptin; Galanin like peptide In certain embodiments, the pharmacologic agent that is administered is not an inverse agonist as defined in publication nos. WO 2005/034871 and WO 2005/035731, such that it is not a substance that has an affinity for the inactive state of a receptor and thereby stabilizes the inactive state of the receptor, or a substance, including, but not limited to, drugs, hormones, or neurotransmitters, that produces inactivation of receptors and/or prevents or hinders activation by agonists, thereby reducing signaling from those receptors. In certain embodiments, the agent is not nadolol, bupranolol, butoxyamine, carazolol, carvedilol, ICI-118, 551, levobunolol, metoprolol, propranolol, sotalol, and timolol, and the salts, solvates, analogues, congeners, bioisosteres, hydrolysis products, metabolites, precursors, and prodrugs thereof. In certain embodiments, the agent is not a "pressor" agent, such that it does not increase blood pressure.

Administering a Pharmacological Agent

In certain embodiments, the subject invention includes administering an effective amount of a pharmacological agent to a subject. Any suitable pharmacological agents may be administered. That is, embodiments of the subject methods include administering an effective amount, i.e., a therapeutically effective amount, of one or more pharmacological agents to a subject. By "effective amount" is meant a dosage sufficient to cause the subject to mount a compensatory response effective to treat the subject, as desired. The effective amount will vary with the age and physical condition of the subject, severity of the condition being treated, the duration of the treatment, the nature of any concurrent treatment, the pharmaceutically acceptable carrier used if any, and analogous factors within the knowledge and expertise of those skilled in the art.

In certain embodiments, more than one type of agent may be administered at the same or different times to treat the same or different condition. The effective amount of a given agent may vary somewhat from subject to subject, and may depend upon factors such as, but not limited to, the age and condition of the subject, the form of the agent, the route and method of delivery, etc., as noted above. Dosages may be determined in accordance with routine pharmacological procedures known to those skilled in the art.

Depending on the particular agent(s) administered to a subject, the agent(s) may be administered to a subject using any convenient means. Thus, a pharmacological agent may be incorporated into a variety of formulations for administration to a subject. A pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the one or more pharmacological agents and other optional ingredients of the subject pharmaceutical agent compositions in that a pharmaceutically acceptable carrier may be combined with the pharmacological agent(s) without eliminating the biological or therapeutically effective activity of the one or more pharmacological agents, and is suitable for use in subjects as provided herein without undue adverse side effects (such as toxicity, irritation, allergic response, and death). Side effects are "undue" when their risk outweighs the benefit provided by the pharmaceutical agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agents employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperitoneal, transdermal, intracheal, intravaginal, endocervical, intrathecal, intranasal, intravesicular, in or on the eye, in the ear canal, etc., administration. In certain embodiments, one or more pharmacological agents may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

Embodiments may include pharmacological agent formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological agent formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an aqueous or non-aqueous liquid; or as an oil-in-water or water-in-oil emulsion. Such pharmacological agent formulations may be prepared by any suitable method of pharmacy which includes, but is not limited to, bringing into association the active pharmacological agent and a suitable carrier (which may contain one or more optional ingredients as noted above). For example, pharmacological agent formulations for use with the subject invention may be prepared by uniformly and intimately admixing the active pharmacological agent(s) with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

Pharmacological agents may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more pharmacological agent(s) made into suppositories by mixing with a variety of bases such as emulsifying bases or water-soluble bases.

Pharmacological agents may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include at least one pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, the one or more pharmacological agents may be utilized in aerosol formulation or an analogous formulation to be administered via inhalation or analogous means. The one or more pharmacological agents employed in the practice of the present invention may be formulated into pressurized acceptable propellants such as dichlorodifluoromethane, propane, nitrogen and the like.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient.

Pharmacological agents may be provided as a salt and may be formed with one or more acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological agents may administered parenterally, such as intravenous (IV) administration, and may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological agent formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

Pharmacological agents may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include one or more pharmacological agents administered as liposomal formulations of the pharmacological agents. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

A pharmaceutical composition of the subject invention may optionally contain, in addition to a pharmacological agent, at least one other therapeutic agent useful in the treatment of a condition. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, anti-fungal, anti-tumor, anti-viral agents, anti-neurodegenerative, and anti-psychotic agents and the like, pharmacological agents may be administered by any method and route of administration suitable to the treatment of the condition, typically as pharmaceutical compositions.

Pharmacological agents may include compositions that may be prepared from water-insoluble compounds, or salts thereof, such as aqueous base emulsions. In such embodiments, the pharmacological agent composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agents, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

In certain embodiments, a pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological agent formulations include, but are not limited to, formulations that include one or more active pharmacological agents and physiological saline solution (optionally including other typical ingredients such as other active agents and buffers).

As noted above, in pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle. The specifications for the unit dosage forms of pharmacological agents of the present invention depend on, for example, the particular pharmacological agent(s) employed and the effect to be achieved, the pharmacodynamics associated with the particular pharmacological agent(s) in the subject, etc.

Embodiments include administering an effective amount of a first agent and an effective amount of a second agent. For example, embodiments may include administering a first agent and a second agent to provide an enhanced therapeutic effect. By "enhanced therapeutic effect" is meant that at least the desired outcome occurs more quickly and/or is of greater magnitude with a combination of the pharmacological agents, as compared to the same doses of each component given alone; or that doses of one or all component(s) are below what would otherwise be a minimum effective dose (a "sub-MED").

Any two pharmacological agents may be given in close enough temporal proximity to allow their individual therapeutic effects to overlap. For example, embodiments of the subject invention include the co-timely administration of a first and second agent, where "co-timely" is meant administration of a second pharmacological agent while a first pharmacological agent is still present in a subject in a therapeutically effective amount. It is to be understood that in some instances this will require sequential administration. Alternatively, multiple routes of administration may be employed, e.g., intravenous or subcutaneous injection combined with oral administration, and the like.

Embodiments also include pharmaceutical compositions in unit dosage forms that are useful which contain more than one type of pharmacological agent. In other words, a single agent administration entity may include two or more pharmacological agents. For example, a single tablet, capsule, dragee, trocheem suppository, syringe, and the like, combining two or more pharmacological agents would be a unit dosage form. The therapeutic agents present in a unit dosage form may be present in amounts such that, upon administration of one or more unit doses of the composition, a subject experiences, e.g., a longer lasting efficacy than with the administration of either agent alone and/or greater magnitude and/or quicker lowering of action. Such compositions may be included as part of a therapeutic package in which one or more unit doses are placed in a finished pharmaceutical container. Labeling may be included to provide directions for using the composition according to the invention. The actual amounts of each agent in such single unit dosage forms may vary according to the specific compositions being utilized, the particular compositions formulated, the mode of application, the particular route of administration, and the like, where dosages for a given subject may be determined using conventional considerations, e.g., by customary comparison of the differential activities of the subject compositions and of a known agent, or by means of an appropriate, conventional pharmacological protocol.

Applying Electrical Energy

As noted above, certain embodiments include employing electrical modulation, in a manner effective to cause the desired enhancement according to the subject methods.

Any suitable area may be targeted for electrical modulation. Areas that may be targeted include, but are not limited to, pre- and post ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynaptic neurons.

As such, areas which may be targeted with electrical energy include, but are not limited to, pre- and post ganglionic nerve fibers, ganglionic structures, efferent and afferent nerve fibers, the hypothalamus, receptors any receptor described herein, afferent autonomic nerves (sympathetic and parasympathetic). Embodiments include receptors of the hypothalamus, including hormonal receptors on the hypothalamus. In certain embodiments, a given nerve fiber or the like may be targeted for electrical modulation in more than one area of the nerve fiber. Targeted areas of the nervous system which may be targeted in accordance with the subject invention include, but are not limited to, vagus nerve, optic ganglion, and sphenopalatine ganglion, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion; superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; and the like, or a combination of two or more of the above.

A number of different devices may be employed in accordance with the subject invention. For example, device and systems for applying electrical energy to a subject and which may be adapted for use in the subject invention are described, e.g., in copending U.S. patent application Ser. Nos. 10/661,368, 10/871,366 and elsewhere, the disclosures of the US patent applications are herein incorporated by reference. Such devices may be positioned directly on a targeted area, e.g., positioned below the skin of a subject directly on or adjacent a portion of the nervous system (e.g., one or more nerve fibers) such as an implantable device, or may be an external device (i.e., some or all of the device may be external to the subject). In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed.

The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output may be provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed).

A controller or programmer may also be coupled with an electric energy applying device. The programmer is typically one or more microprocessors under the control of a suitable software program. Other components of the programmer will be apparent to those of skill in the art, e.g., analog to digital converter, etc. The electric energy applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

FIG. 1 shows an exemplary embodiment of an electric energy applying device 100. Device 100 may be implanted in a suitable position of a subject's body 10. One or more leads 23 are shown positioned to stimulatory or inhibitory electrical energy. Device 100 include energy source 14 which may take the form of a modified signal generator, Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more delivery elements such as stimulation electrodes which may be implanted using conventional surgical techniques. The type of treatment that is desired determines the location of the electrodes. Any number of electrodes may be used for various applications. Each of the electrodes may be individually connected to energy source 14 through lead 23 and conductors 16 and 18. Lead 23 may be surgically implanted either by a laminotomy or by a needle.

Energy source or signal generator 14 may be programmed to provide a predetermined stimulation (or inhibition) dosage in terms of pulse amplitude, pulse width, pulse frequency, or duty cycle. As shown, a programmer 20 may be utilized to provide stimulation (or inhibition) parameters to the delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10. For example, in certain embodiments the programmer may be integrated with the energy source, electrode, etc., for example as a single unit.

Device 100 may optionally include one or more sensors to provide closed-loop feedback control of the treatment and/or electrode positioning. One or more sensors (not shown) may be attached to or implanted into a portion of a subject's body suitable for detecting a physical and/or chemical indicator of the subject. For example, sensing feedback may be accomplished, e.g., by a mechanical measure within a lead or an ultrasound or other sensor to provide information about the treatment parameters, lead positioning, LTP, etc.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by procedures known in the art, such as have been applied in surgical neuromodulation therapies used to treat Parkinson's disease.

In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above. In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar.

For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if a predetermined detection criteria is not detected the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

Utility

The subject methods find use in a variety of applications, as reviewed above. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

As indicated above, the subject methods may be used in the treatment of a variety of different disease conditions, including, but not limited to: cardiovascular diseases, such as atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, fatal arrythmias, coronary syndromes, coronary vasospasm, sick sinus syndrome, bradycardia, tachycardia, arrhythmias, thromboembolic disease, deep vein thrombosis, coagulopathy, DIC, mesenteric ischemia, syncope, venous thrombosis, arterial thrombosis, malignant hypertension, secondary hypertension, primary pulmonary hypertension, secondary pulmonary hypertension, Raynaud's, paroxysmal supraventricular tachycardia, and the like; neurodegenerative diseases, such as Alzheimer's, Pick's, Parkinson's, amyotrophic lateral sclerosis, neuroinflammatory diseases, viral meningitis, viral encephalitis, fungal meningitis, fungal encephalitis, multiple sclerosis, charcot joint, schizophrenia, and the like; orthopedic inflammatory diseases, such as osteoarthritis, reflex sympathetic dystrophy, osteoporosis, regional idiopathic osteoporosis, Paget's disease, juvenile chronic arthritis, antigen-induced arthritis, and the like; inflammatory conditions, such as ARDS, multiple sclerosis, rheumatoid arthritis, migraines, chronic headaches, and the like; lymphoproliferative diseases, such as lymphoma, lymphoproliferative disease, Hodgkin's disease, inflammatory pseudotumor of the liver, and the like; autoimmune diseases, such as Graves disease, Hashimoto's, Takayasu's disease, Kawasaki's disease, arteritis, scleroderma, CREST syndrome, allergies, dermatitis, Henoch-Schlonlein purpura, goodpasture syndrome, autoimmune thyroiditis, myasthenia gravis, lupus, Reiter's syndrome and the like; inflammatory and infectious diseases, such as sepsis, diseases of wound healing, viral infections, wound healing, tuberculosis, infection, fungal infections, AIDS, human immunodeficiency virus and the like; pulmonary diseases, such as tachypnea, fibrotic lung diseases, cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like, gastrointestinal disorders, such as hepatitis, xerostomia, bowel mobility, constipation, irritable bowel syndrome, peptic ulcer disease, ileus, post-operative bowel dysmotility, inflammatory bowel disease, typhlitis, cholelithiasis, cholestosis, fecal incontinence, cyclic vomiting syndrome, diverticulitis/diverticulosis, and the like; endocrine disorders, such as hypothyroidism, diabetes, obesity, syndrome X, hyperglycemia, insulin resistance, PCOS, and the like; genitourinary disorders, such as bladder dysfunction, renal failure, erectile dysfunction, hyperreninemia, hepatorenal syndrome, pulmonary renal syndrome, incontinence, arousal disorders, menopausal mood disorders, premenstrual mood disorders, and the like; skin disorders, such as wrinkles, cutaneous vasculitis, and the like; aging associated diseases and conditions, such as shy dragers, multi-symptom atrophy, age related inflammation conditions, cancer, aging and the like; Th-2 dominant, such as diseases typhlitis, osteoporosis, lymphoma, myasthenia gravis, lupus and the like; conditions that cause hypoxia, hypercarbia, and/or acidosis, such as COPD, emphysema, any chronic lung disease that causes acidosis, sudden infant death syndrome, sudden adult death syndrome, acute pulmonary embolism, chronic pulmonary embolism, pleural effusion, cardiogenic pulmonary edema, non-cardiogenic pulmonary edema, acute respiratory distress syndrome ("ARDS"), neurogenic edema, acidosis of any causehypercapnia, acidemia, renal tubular acidosis, asthma, any chronic lung disease that causes hypoxia or hypercarbia or hypercapnia, and the like; Neurologic diseases, such as epilepsy, seizures, stroke, insomnia, sleep disorders, cerebral vascular accident, transient ischemic attacks, headaches, concussions, post-concussive syndrome, cerebral vascular, vasospasm, central sleep apnea, obstructive sleep apnea, stress, bipolar disorder, migraines, chronic headaches, ADEM, depression, and the like; pediatric conditions, e.g., respiratory distress syndrome, sudden infant death syndrome, Hirschsprung's disease, bronchopulmonary dysplasia, congenital megacolon, aganglionosis, juvenile rheumatoid arthritis, juvenile chronic arthritis and the like; OB-GYN diseases, e.g., amniotic fluid embolism, pregnancy-related arrhythmias, fetal stress, fetal hypoxia, amniotic fluid embolism, gestational diabetes, preterm labor, cervical incompetence, fetal distress, peri-partum maternal mortality, labor complications, premenstrual syndrome, dysmenorrhea, endometriosis, and the like; as well as other conditions, including but not limited to: chronic pain, glaucoma, trauma, hospitalization, post-operative recovery, post-procedural recovery, transplant-related side effects, fibrosis, transplant-related tachycardia, transplant rejection, transplant-related bowel dysmotility, transplant-related hyperreninemia, male infertility, disorders of thermoregulation, fibromyalgia, and the like; menstrual related disorders, e.g., pelvic pain, dysmenorrhea, gi disease, nausea, etc.; peripartum and pregnancy related disorders; peripartum cardiomyopathy; sickle cell disease; reperfusion injury; central serous choroidoretinopathy; stress; post traumatic stress disorder; gulf war syndrome; etc.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a pharmacological agent to a subject, e.g., programming may be configured to determine suitable dosage, etc. In certain embodiments programming may control a device to administer electrical energy to a subject, e.g., may control the activation/termination of electrical energy including selecting suitable electrical parameters. Programming may be configured to, or otherwise be capable of, directing a microprocessor to activate, i.e., turn "on" and "off" an electric energy applying device for applying energy to a subject. For example, if so determined, the processor may direct the electric energy applying device to provide the appropriate energy to result in the desired action. Accordingly, a processor may select the appropriate parameters (e.g., frequency, amplitude, etc.) depending on what is required and direct an electric energy applying device to implement the parameters.

Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include an electric energy applying device, as described above. Devices for delivering, e.g., implanting, an electric energy applying device to a target site of a subject such as into the body cavity of a subject may also be included in the subject kits. For example, an endoscope, introducer needle, and the like may be provided. The subject kits may also include one or more pharmacological agents, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrode, etc.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

REPRESENTATIVE EMBODIMENTS

In further describing the subject invention, a number of representative embodiments are described below in greater detail.

Implantable Drug Delivery Devices

In one representative embodiment, the subject methods include applying a pharmacological stimulus from an implantable drug delivery device in a manner effective to provide for the desired compensatory response in the subject. A feature of certain of these embodiments is that the implantable device delivers drug in a manner effective to cause the subject in which the device is implanted to mount the desired compensatory response, as described above. In certain embodiments, the implantable devices deliver agent to the subject in which they are implanted in a manner that is discontinuous or pulsed, so as to achieve the desired stimulus of limited temporal duration.

Any of a variety of controlled drug delivery devices can be used in these embodiments of the present invention to accomplish delivery of a drug formulation according to the subject invention. In general, the drug delivery device minimally comprises a controlled drug delivery device and, in one embodiment, further comprises a drug delivery catheter, e.g., where the implantation site is distant from the delivery site.

Drug delivery devices suitable for use with the present invention can take advantage of any of a variety of controlled drug release devices. In general, the drug release devices suitable for use in the invention comprise a drug reservoir for retaining a drug formulation or alternatively some substrate or matrix which can hold drug (e.g., polymer, binding solid, etc.). The drug release device can be selected from any of a variety of implantable controlled drug delivery system known in the art. Controlled drug release devices suitable for use in the present invention generally can provide for delivery of the drug from the device at a selected or otherwise patterned amount and/or rate to a selected site in the subject.

In representative embodiments, implantable infusion devices include a generally disc-shaped housing having a diameter dimension and a thickness dimension. The thickness dimension of the device is dependent, at least in part, upon the relative placement of device components and the thickness dimensions of the device components. Such devices typically include a reservoir located within the housing for holding a volume of an infusion medium, for example, a liquid medication. Such devices also typically include an inlet for receiving infusion medium into the reservoir to fill or re-fill the reservoir, for example, from a hollow needle, such as a syringe needle.

In addition, implantable infusion devices may include a driving mechanism, such as a pump, for controlling the flow of infusion medium from the reservoir to the patient, through an outlet in the housing, either on a continuous basis, at scheduled or programmed times or in response to signals from a sensor or other signal source. Other devices include pressurized gas sources for driving infusion medium from the reservoir. Each of those components define a thickness dimension which, depending upon their placement on the device, may affect the overall thickness dimension of the implantable infusion device.

Example implantable infusion devices are described in U.S. Pat. No. 5,527,307, U.S. Pat. No. 5,514,103 and U.S. Pat. No. 5,176,644, each to Srisathapat et al. (and assigned to Minimed Technologies, Ltd.), U.S. Pat. No. 5,167,633 to Mann et al. (and assigned to Pacesetter Infusion, Ltd), U.S. Pat. No. 4,697,622 to Swift (assigned to Parker Hannifin Corporation) and U.S. Pat. No. 4,573,994 to Fischell et al. (assigned to The Johns Hopkins University), each of which is incorporated herein by reference. Each of the above-cited patents describes an implantable infusion device which includes a generally disc-shaped housing containing a reservoir, a driving mechanism or pump, an inlet, an outlet and an electronic circuit for controlling the operation of the driving mechanism or pump.

In certain embodiments, the infusion pump employed is part of a "closed-loop" system. The infusion pump system according to these embodiments of the invention employs a pump for delivering measured doses of an infusion formulation. In one embodiment, the pump comprises an electromagnetic mechanism that is activated to selectively drive infusion formulation to the user. The pump may be activated according to a programmed dispensing rate or schedule, or according to an actuation signal from a sensing device, timer, manual operator or other suitable means. In certain embodiments, the pump may be activated by a control signal communicated to the pump from a computing element which may be included in the infusion pump system.

The infusion pump system according to these embodiments of the invention further employs a sensing device for monitoring a selected biological state.

The infusion pump system according to these embodiments of the invention further employs a computing element which may, along with other pump control functions, execute a closed-loop algorithm which may continuously adjust infusion formulation delivery as a function of the sensed biological state. The computing element may comprise one or more programmable processors, logic circuits, or other hardware, firmware or software components configured for implementing the control functions described herein.

The infusion pump system according to certain embodiments of the invention further employs a communication device for communicating user-initiated signals to the computing element. The user-initiated signals may be representative of events that affect the selected biological state. In one embodiment, the communication device communicates with the computing element via a radio frequency ("RF") transceiver. However, in other embodiments other suitable means of data communication may be employed, such as, for example, ultrasonics.

Representative closed-loop systems of interest are described in: U.S. Pat. Nos. 6,827,702; 6,740,072 and 6,558,351; the disclosures of which are herein incorporated by reference.

In some embodiments, the delivery device is one that is adapted for delivery of an agent over extended periods of time, such as discontinuously over extended periods of time. Such delivery devices may be adapted for administration of an agent for several hours (e.g., 2 hours, 12 hours, or 24 hours to 48 hours or more), to several days (e.g., 2 to 5 days or more, from about 100 days or more) to several months or years, with intermissions of non-delivery, e.g., referred to as holiday periods above. As such, the devices are configured to deliver a discontinuous or pulsed delivery of an agent over an extended period of time, where the pulsed delivery may in certain embodiments, be characterized as "irregularly irregular" as described above.

Release of drug from the device, particularly controlled release of drug, can be accomplished in any of a variety of ways according to methods well known in the art, e.g., by incorporation of drug into a polymer that provides for substantially controlled diffusion of drug from within the polymer, incorporation of drug in a biodegradable polymer, providing for delivery of drug from an osmotically-driven device, etc. Where the drug delivery device comprises a drug delivery catheter, drug can be delivered through the drug delivery catheter to the delivery site as a result of capillary action, as a result of pressure generated from the drug release device, by diffusion, by electrodiffusion or by electroosmosis through the device and/or the catheter.

The drug delivery device must be capable of carrying the drug formulation in such quantities and concentration as therapeutically required, and must provide sufficient protection to the formulation from attack by body processes for the duration of implantation and delivery. The exterior is thus preferably made of a material that has properties to diminish the risk of leakage, cracking, breakage, or distortion so as to prevent expelling of its contents in an uncontrolled manner under stresses it would be subjected to during use, e.g., due to physical forces exerted upon the drug release device as a result of movement by the subject or physical forces associated with pressure generated within the reservoir associated with drug delivery. The drug reservoir or other means for holding or containing the drug must also be of such material as to avoid unintended reactions with the active agent formulation, and is preferably biocompatible (e.g., where the device is implanted, it is substantially non-reactive with respect to a subject's body or body fluids).

Suitable materials for the reservoir or drug holding for use in the delivery devices of the invention are well known in the art. For example, the reservoir material may comprise a non-reactive polymer or a biocompatible metal or alloy. Suitable polymers include, but are not necessarily limited to, acrylonitrile polymers such as acrylonitrile-butadiene-styrene polymer, and the like; halogenated polymers such as polytetrafluoroethylene, polyurethane, polychlorotrifluoroethylene, copolymer tetrafluoroethylene and hexafluoropropylene; polyethylene vinylacetate (EVA), polyimide; polysulfone; polycarbonate; polyethylene; polypropylene; polyvinylchloride-acrylic copolymer; polycarbonate-acrylonitrile-butadiene-styrene; polystyrene; cellulosic polymers; and the like. Further exemplary polymers are described in The Handbook of Common Polymers, Scott and Roff, CRC Press, Cleveland Rubber Co., Cleveland, Ohio.

Metallic materials suitable for use in the reservoir of the drug release device include stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys.

Exemplary materials for use in polymeric matrices include, but are not necessarily limited to, biocompatible polymers, including biostable polymers and biodegradable polymers. Exemplary biostable polymers include, but are not necessarily limited to silicone, polyurethane, polyether urethane, polyether urethane urea, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Exemplary biodegradable polymers include, but are not necessarily limited to, polyanhydrides, cyclodestrans, polylactic-glycolic acid, polyorthoesters, n-vinyl alcohol, polyethylene oxide/polyethylene terephthalate, polyglycolic acid, polylactic acid and other related bioabsorbable polymers.

Where the drug formulation is stored in a reservoir comprising metal or a metal alloy, particularly titanium or a titanium alloy having greater than 60%, often greater than 85% titanium is preferred for the most size-critical applications, for high payload capability and for long duration applications and for those applications where the formulation is sensitive to body chemistry at the implantation site or where the body is sensitive to the formulation. Most preferably, the drug delivery devices are designed for storage with drug at room temperature or higher.

Drug release devices suitable for use in the invention may be based on any of a variety of modes of operation. For example, the drug release device can be based upon a diffusive system, a system that employs positive pressure, etc. For example, the drug release device may be based upon an electrodiffusion system, an electrolytic pump, an effervescent pump, a piezoelectric pump, a hydrolytic system, etc.

Drug release devices based upon a mechanical or electromechanical infusion pump, can also be suitable for use with the present invention. Examples of such devices include those described in, for example, U.S. Pat. Nos. 4,692,147; 4,360,019; 4,487,603; 4,360,019; 4,725,852, WO 97/27840 and U.S. Pat. Nos. 5,985,305 and 5,728,396; and the like.

In one embodiment, the drug release device is a controlled drug release device in the form of an osmotically-driven device. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments it may be desirable to provide a drug delivery catheter with the drug delivery device, e.g., where the implantation site and the desired delivery site are not the same or adjacent. The drug delivery catheter is generally a substantially hollow elongate member having a first end (or "proximal" end) associated with the drug release device of the drug delivery device, and a second end (or "distal" end) for delivery of the drug-comprising formulation to a desired delivery site. Where a drug delivery catheter is used, a first end of the drug delivery catheter is associated with or attached to the drug delivery device so that the lumen of the drug delivery catheter is in communication with the drug reservoir in the drug delivery device, so that a formulation contained in a drug reservoir can move into the drug delivery catheter, and out a delivery outlet of the catheter which is positioned at the desired delivery site.

The body of the catheter defines a lumen, which lumen is to have a diameter compatible with providing leak-proof delivery of drug formulation from the drug delivery device. The body of the catheter can be of any of a variety of dimensions and geometries (e.g., curved, substantially straight, tapered, etc.) that can be selected according to their suitability for the intended site for drug delivery. The distal end of the drug delivery catheter can provide a distinct opening for delivery of drug, or as a series of openings.

The drug delivery catheter may be produced from any of a variety of suitable materials, and may be manufactured from the same or different material as the reservoir of the drug release device. Impermeable materials suitable for use in production of the controlled drug release device as described above are generally suitable for use in the production of the drug delivery catheter. Exemplary materials from which the drug delivery catheter can be manufactured include, but are not necessarily limited to, polymers; metals; glasses; polyolefins (high density polyethylene (HDPE), low density polyethylene (LDPE), linear low density polyethylene (LLDPE), polypropylene (PP), and the like); nylons; polyethylene terephthalate; silicones; urethanes; liquid crystal polymers; PEBAX®; HYTREL®; TEFLON®; perfluoroethylene (PFE) perfluoroalkoxy resins (PFA); poly(methyl methacrylate) (PMMA); multilaminates of polymer, metals, and/or glass; nitinol; and the like.

The drug delivery catheter can comprise additional materials or agents (e.g., coatings on the external or internal catheter body surface(s)) to facilitate placement of the drug delivery catheter and/or to provide other desirable characteristics to the catheter. For example, the drug delivery catheter inner and/or outer walls can be coated with silver or otherwise coated or treated with antimicrobial agents, thus further reducing the risk of infection at the site of implantation and drug delivery.

Treatment of a Subject for Hypertension with an Implantable Drug Delivery Device In certain embodiments, a subject is treated for hypertension using an implantable drug delivery device. In these embodiments, the drug delivery device delivers a prohypertensive, e.g., sympathetic bias enhancing, agent in a manner effective to cause the subject to mount a compensatory response, e.g., in the form of a long-term decrease in sympathetic bias.

A variety of prohypertensive agents are known and may be employed. Representative prohypertensive agents include, but are not limited to: Aldosterone, Alpha agonists, angiotensin agonists, calcium channel agonists, corticotropin agonists, anti-diuretics, dopamine agonists, epinephrine and norepinephrine agonists, glucocorticoid agonists, mineralocorticoid agonists, oxycontin agonists, renin agonists, and vasopressin agonists. Representative agents for each of these classes are provided in Appendix B of U.S. Provisional Patent Application No. 60/650,192, the disclosure of which is herein incorporated by reference. In addition, representative agents for each of these classes are found in Pharmaprojects, published by PJB Publishing, Version 5.0, London UK (November, 2004).

In certain embodiments, the agent employed has sympathetic bias enhancing activity. By sympathetic bias enhancing activity, it is meant that the agent, when administered to a subject, produces an increase in the sympathetic bias of the subject. Specifically, the agent causes the ratio of sympathetic activity to parasympathetic activity in the subject to be increased. Methods of determining sympathetic activity and parasympathetic activity in a subject are known in the art. A given agent is considered to be a sympathetic bias enhancing agent if, upon administration to a subject, it causes an increase in the ratio of sympathetic to parasympathetic activities of at least about 2-fold, such as at least about 5-fold, including at least about 10-fold.

As indicated above, the agent is administered to a subject in a manner effective to cause the subject to mount a compensatory response effective to treat the hypertension. In representative embodiments, the sympathetic bias enhancing agent is administered to the subject in a manner such that a short term increase in sympathetic bias in the subject is achieved that results in the production of a long term decrease in sympathetic bias in the subject. The increase and decrease in sympathetic bias referred to above is in reference to the sympathetic bias prior to administration of the agent. In general the magnitude of the increase and decrease is at least about 2-fold, such as at least about 5-fold, including at least about 10-fold. In the most general sense, the phrases "short term" and "long term" as used herein are relative to each other, where the duration of sympathetic bias increase is considered short term if it is shorter than the resultant duration of sympathetic bias decrease, e.g., by at least 1 day, such as by at least 1 week, including by at least 1 month. In representative embodiments, short term increase in sympathetic bias has a duration of at least about 1 second, such as at least about 1 minute, including at least about 30 seconds, but lasts no more than about 2 hours, including no more than about 90 minutes, such as no more than about 60 minutes. In representative embodiments, the long term decrease in sympathetic bias has a duration of at least about 1 second, such as at least about 12 hours, including at least about 1 hour, where the duration may be as long as 5 years or longer, including as long as 1 month or longer.

In certain embodiments, the short term increase in sympathetic bias is achieved by administering the agent in a manner such that the agent is active for only a short duration, where by short duration is meant that the applied stimulus lasts for less than about 1 week, e.g., less than about 3 days, e.g., less than about 1 day, e.g., less than about 12 hours, where the duration of the applied stimulus may be even shorter.

Following delivery of the agent from the implanted device, the subject is permitted to mount a compensatory response, e.g., in the form of a long term decrease in sympathetic bias. In this step of the subject methods, no additional sympathetic bias enhancing agent is administered to the subject. The duration of this period, which may be a period between agent administration (depending on the particular embodiment), may vary. However, in representative embodiments, this period, which may be referred to as a "holiday" period, is at least about 1 day, such as at least about 2 days, including at least about 5 days, at least about 10 days, at least about 15 days, or longer.

In certain embodiments, the methods include close monitoring or supervision of the subject during and/or after administration of the agent. This monitoring may be completely automated, or at least in part performed manually, e.g., by a health care professional. For example, a health care professional can closely watch the subject following administration of the agent as well as during the holiday period following agent administration, and based on this monitoring determine when a next dosage of agent should be delivered. Monitoring also assures that the sympathetic bias enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with an agent delivery device, such that the system, based on monitored parameters, determines when next to administer a dose of agent, the dosage of the next dose, etc. As such, the method may be characterized as administering a first dose to the subject and monitoring the subject for a response thereto. Following this first step, the method further includes administering at least a second dose to the subject, wherein the second dose is determined based on the monitored response to the first dose.

In certain embodiments, doses of agent are administered to the subject in an "irregularly irregular" manner. As such, dosages and timing thereof, as well as duration of holiday periods between such events, varies randomly over the entire course of a treatment, or at least a portion thereof. In addition, the variation does not follow any pattern, but instead is random.

Treatment of a Subject for Hypertension with an Implantable Electrostimulatory Device In certain embodiments, a subject is treated for hypertension using an implantable electrostimulatory device. In these embodiments, the electrostimulatory device delivers an electrical stimulus to a target site(s) of a subject in a manner effective to cause the subject to mount a compensatory response, e.g., in the form of a long-term decrease in sympathetic bias.

In certain embodiments, the implantable device is operated in a manner that produces a sympathetic bias in a subject, as described above. In certain embodiments, the short term increase in sympathetic bias is achieved by applying the stimulus in a manner such that the agent is active for only a short duration, where by short duration is meant that the applied stimulus lasts for less than about 1 week, e.g., less than about 3 days, e.g., less than about 1 day, e.g., less than about 12 hours, where the duration of the applied stimulus may be even shorter.

Following delivery of the agent from the implanted device, the subject is permitted to mount a compensatory response, e.g., in the form of a long term decrease in sympathetic bias. In this step of the subject methods, no additional stimulus is applied to the subject. The duration of this period, which may be a period between stimulus application (depending on the particular embodiment), may vary. However, in representative embodiments, this period, which may be referred to as a "holiday" period, is at least about 1 day, such as at least about 2 days, including at least about 5 days, at least about 10 days, at least about 15 days, or longer.

In certain embodiments, the methods include close monitoring or supervision of the subject during and/or after administration of the agent. This monitoring may be completely automated, or at least in part performed manually, e.g., by a health care professional. For example, a health care professional can closely watch the subject following stimulus application as well as during the holiday period following agent administration, and based on this monitoring determine when a next stimulus should be applied. Monitoring also assures that the sympathetic bias enhancement is not so severe as to be ultimately damaging to the subject at an unacceptable level. Certain aspects of the monitoring may be automated. For example, following stimulus application, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with the stimulatory device, such that the system, based on monitored parameters, determines when next to administer a dose of agent, the dosage of the next dose, etc. As such, the method may be characterized as administering a first stimulus to the subject and monitoring the subject for a response thereto. Following this first step, the method further includes administering at least a second stimulus to the subject, wherein the second stimulus is determined based on the monitored response to the first stimulus.

In certain embodiments, doses of agent are administered to the subject in an "irregularly irregular" manner. As such, dosages and timing thereof, as well as duration of holiday periods between such events, varies randomly over the entire course of a treatment, or at least a portion thereof. In addition, the variation does not follow any pattern, but instead is random.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Example of Paradoxical Pulsed Therapy Using Neurostimulation

One example of utilizing pulsed paradoxical therapy for the treatment of hypertension includes using an implanted neurostimulation device or combination of devices with pulsed stimulation of autonomic nerves. This device induces intermittent electrical stimulation of sympathetic nerves to induce short intervals of increased blood pressure ranging from seconds to hours to increase dynamic range. Alternatively, or in addition, this device induces intermittent electrical stimulation of parasympathetic nerves to induce short intervals of decreased blood pressure ranging from seconds to hours to increase dynamic range. In addition, one could use measured feedback to regulate the frequency and duration of pulsed therapies.

A. Dog Studies

Example Study 1:

Effect of Paradoxical Pulsed Neurostimulation Therapy in Hypertensive Dogs

Double-blinded randomized controlled studies are performed in a set of dogs with experimentally induced hypertension to demonstrate that intermittent electrical stimulation of sympathetic nerves lowers blood pressure. Experiments are conducted on mongrel dogs of either sex weighing 14-17 kg. Dogs are prepared for study by being treated for ectoparasites and endoparasites in addition to being immunized for parvovirus, canine distemper, hepatitis, parainfluenza, and coronavirus. All experiments are conducted in accordance with the National Institutes of Health Guide for the Care and Use of Laboratory Animals. Dogs are fed a low sodium diet supplemented with sodium chloride to achieve a sodium intake of 40 mmol/d (normal sodium intake). This dietary regimen provides a constant and known level of dietary sodium intake. Throughout the experimental protocol, all dogs are allowed water ad libidum.

For implantation of the neurostimulation devices, dogs are anesthetized with sodium thiamylal (30 mg/kg IV) for induction and then halothane (1%). Sympathetic nerves in candidate plexi are isolated and affixed to bipolar stimulating electrodes. Catheters are inserted via the femoral vessels into the aorta for direct arterial pressure measurement. All catheter lines are tunneled subcutaneously to the midscapular region of the back and exteriorized. A 10-day steady state control period precedes the experimental period for all subjects to allow for recovery from surgical instrumentation.

Throughout the experimental period, dogs in the treatment group initially receive pulsed stimulation with pulse duration ranging from about 1 to about 10800 seconds at a frequency no less than 1 to about 1440 pulses per day. Dogs in the control group receive no stimulation during the experimental period. Measurement of systolic, diastolic, and mean arterial blood pressures are obtained via pressure transducer on an ongoing basis. Measurements continue for a recovery period of 15 days following completion of pulsed administration.

In accordance with changes in the measured parameters, the schedule of administration of pulses is actively modified in the following manner: for any increase in systolic pressure of greater than 1-10 mm Hg or diastolic pressure of greater than 1-10 mm Hg, the frequency of administration of pulses is decreased by 1-1440 per day and/or the duration of each pulse is decreased by 1-10800 seconds. For any decrease in systolic pressure of greater than 1-10 mm Hg or diastolic pressure of greater than 1-10 mm Hg, the frequency of administration of pulses is increased by 1-1440 per day and/or the duration of each pulse would be increased by 1-10800 seconds.

In order to assess potential effects in other systems where sympathetic activity typically exerts influence, arterial blood samples and pulmonary function tests are obtained on a weekly schedule where the following parameters may be assessed:

|  | Test | Reference value | Claimed Range |
|---|---|---|---|
| pulmonary gas serum blood gas | Alveolar oxygen | 650-713 mmHg | 600-713 mmHg |
|  | pH | 7.35-7.45 | 7.1 to 7.7 |
|  | arterial pO2 | 80-100 mmHg | 50-110 |
|  | arterial pcO2 | 35-45 mmHg | 10 to 80 |
|  | arterial bicarb | 25-35 meq/L | 10 to 40 |
|  | alveolar/oxygen ratio | 0.8 | 1 to 0.6 |
|  | aa gradient | 10-15 mmHg | 5 to 120 |
|  | venous oxygen sat | 60% | 30-80% |
| cardoipulmonary | cardiac output | 3.5 to 5.5 L/min | 1 to 6 |
|  | cardiac index | 2.8-3.2 L/min/m2 | 0.5 to 6 |
|  | right atrial pressure | 1-7 mmHg | 1 to 30 |
|  | right ventricular systolic pressure | 15-25 mmHg | 5 to 50 |
|  | right ventricular diastolic pressure | 0-8 mm Hg | 1 to 50 |
|  | pulmonary arterial systolic pressure | 15-25 mmHg | 5 to 50 |
|  | pulmonary arterial diastolic pressure | 8-15 mmHg | 1 to 30 |
|  | mean pulmonary arterial pressure | 10-20 mmHg | 5 to 50 |
|  | pulmonary capillary wedge pressure | 6-12 mmHg | 1 to 20 |
| pulmonary function test | tidal volume | 8-15 ml/Kg | 2-20 or 20-80% |
|  | total lung capacity | 5-7 liters | 3 to 10 or 20-120% |
|  | residual volume | 1.5 to 2.5 liters | 0.5 5 or 20-120% |
|  | forced expiratory volume in 1 second | 3.5-4 liters | 0.5 to 6 or 20-120% |
|  | functional vital capacity | 4-6 liters | 0.5 to 6 or 20-120% |
|  | FEV1/FVC ratio | >75% | 20-120% |
|  | forced expiratory flow | 75-125% | 50 to 150% |
|  | peak expiratory flow rate | 80-100% | 60-120% |
|  | forced expiratory time | <5 seconds | 0-20 seconds |
|  | corrected diffusion capacity | 75-80% | 60-140% |
|  | corrected QT interval | <440 | <600 |
| sleep study | sleep latency | >10 min | 0-1 hour |
|  | total sleep time | >5.5 hours | 0-12 hours |
|  | percent rem | >15% of TST | 0-40% total sleep time |
|  | percent stage 3-4 non rem | >25% of TST | 0-50% total sleep time |
|  | respiratory arousal index | <5/hour total sleep time | 0-40/hour total sleep time |
|  | periodic leg movements | <1/hour total sleep time | 0-40/hour total sleep time |
|  | apnea index | <1/hour total sleep time | 0-20/hour total sleep time |
|  | hypopnea index | <3/hour total sleep time | 0-40/hour total sleep time |
|  | nadir oxygen saturatin | >92% | 40-100% |
|  | mean oxygen saturation | >95% | 40-100% |
|  | desaturation index | <5 defined as >4% for 5 seconds/hour of total sleep time | 0-40 defined as >4% for 5 seconds/hour of total sleep time |
|  | highest carbon dioxide | 52 mm Hg | 10-80 mmHg |
|  | carbon dioxide >45 mmHg | <20% of total sleep time | 0-60% of total sleep time |
| Serum Markers | Catecholamine levels |  |  |
|  | Acetycholine levels | 650-1500 IU/L | 300-2000 IU/L |
|  | Aldosterone levels | 17-70 nmol/day | 5-150 nmol/L/day |
|  | Renin levels | 7-76 uU/mL | 3-200 uU/ml |
|  | Vasopressin levels | 2-8 pg/mL | 1-20 pg/ml |
|  | angiotensin converting enzyme levels | 25-100 IU/L | 5-200 U/L |
|  | interleukin 1-3 and 5-13 and 18 | modulate |  |
|  | Interleukin 4 | decrease |  |
|  | interferon alpha and | modulate |  |

-continued

| | Test | Reference value | Claimed Range |
|---|---|---|---|
| | beta interferon gamma | increase | |
| | tumor necrosis factor alpha | modulate | |
| | transforming growth factor | modulate | |
| | hemoglobin A1C | 4-8% | 2-12% |
| | Fasting glucose | 3.5-6.0 mmol/L | 1-10 mmol/L |
| | high density lipoprotein | 45-60 | 10 to 90 |
| | low density lipoprotein | 95-130 | 60-200 |
| | triglyceride | <2 mmol/L | 4 to 4 mmol/L |
| | beta natriuretic peptide | 20-40 pg/mL | 0-100 pg/mL |
| | alpha natriuretic peptide | 20-40 pg/mL | 0-50 pg/mL |
| | erythrocyte sedimentation rate | 0-35 mm/Hour | 1-200 mm/Hour |
| | c reactive peptide | <10 mg/L | 1-80 mg/L |
| | transferrin | 1.75 to 3.13 g/L | 0.5 to 6 g/L |
| | Hemloglobin | 135-160 gm/L | 25 to 300 gm/L |
| | hematocrit | 37-54% | 25-60% |
| | ferritin | 20-240 ug/L | 5 to 600 ug/L |
| | iron | 10-40 umol/L | 5 to 100 umol/L |
| | cholinesterase | 650-1500 IU/L | 200-2500 IU/L |
| | Urine adrenaline | 0-80 nmol/day | 0-200 nmol/day |
| | Urine noradrenaline | 0-780 nmol/day | 0-1600 nmol/day |
| | Urine dopamine | 0-3500 nmol/day | 0-7000 nmol/day |
| | adrenocorticotrophic hormone | <19 pmol/L | 0 to 40 pmol/L |
| | antidiuretic hormone | 2-8 pg/mL | 1-20 pg/mL |
| | thrombin clotting time | 10-20 secs | 5-30 secs |
| | total serum cholesterole | 110-120 | 100-300 |
| Additional | body mass index | 20-30 | <40 |
| | systolic blood pressure | <125 | 90-180 |
| | diastolic blood pressure | <75 | 30-100 |
| | pulse pressure | <20 | 20-40 |
| | heart rate | 60-100 | 30-200 |
| | heart rate variability | increase | |
| | respiratory sinus arrhythmia | increase | |

All dogs in the treatment group are observed to initially have either no changes or statistically negligible increases in systolic, diastolic, and mean arterial pressures while the compensatory response to administration begins to take hold. At some point during the experimental period these dogs are observed to begin to manifest reductions in systolic, diastolic, and mean arterial pressures. The frequency and duration of pulses is gradually increased so as to increase the magnitude of the reduction for the duration of the experimental period. These reductions are maintained upon cessation of the treatment for the duration of the recovery period. Dogs in the control group maintain the same values in these parameters throughout both the control period and the experimental period. No adverse effects of treatment are found in any of these subjects.

Example Study 2

Effect of Paradoxical Pulsed Neurostimulation Therapy in Normotensive Dogs

In double-blinded randomized controlled studies performed in similar fashion to that described in Example 1, the effect of pulsed stimulation of sympathetic nerves on the blood pressure in normotensive dogs is determined. The control period in this case is 10 days and the experimental period 30 days. Again, dogs in the treatment group receive pulsed stimulation of selected sympathetic nerves using implanted bipolar electrodes with pulse duration of from about 1 to about 10800 seconds at a frequency no less than about 1 to about 1440 per day. The schedule of pulse administration is adjusted during the course of the experimental period by the protocol as previously noted. Control subjects have similar devices implanted but do not receive any pulsed stimulation for the duration of the treatment period.

As with the hypertensive dogs, the pulsed electrical stimulation of sympathetic nerves in normotensive dogs results in significant reductions in mean arterial pressures maintained upon cessation of treatment. Dogs in the control group maintain the same mean arterial pressure throughout both the control period and the experimental period. Findings of reduction in normotensive dogs show that paradoxical pulsed therapy readily finds prophylactic use in preventing the onset of hypertension in individuals identified as predisposed to the condition.

B. Human Studies

Example Study 1:

Effect of Paradoxical Pulsed Neurostimulation Therapy in Hypertensive Patients

Double-blinded randomized controlled studies are performed in a set of patients with essential hypertension to demonstrate that intermittent electrical stimulation of sympathetic nerves lowers blood pressure. In all patients, hypertension is confirmed on at least three occasions in an outpatient setting after the patient has been sitting for at least 10 minutes. Blood pressure ranges recorded indicate elevation of both systolic and diastolic components of the blood pressure. No patients have clinical signs or symptoms of pheochromocytoma or renal artery stenosis, and no patients have clinical or laboratory evidence of impaired cardiac, renal, pulmonary, or hepatic function. Urinalysis and serum concentrations of creatinine, sodium, and potassium are confirmed to be within normal limits for patients.

All medications are stopped for each individual for at least four weeks before the beginning of the study. All patients remain hospitalized throughout the study, where physical activity consists of only daily walks. Throughout the study, each patient ingests a constant amount of a nutritionally adequate whole-foods diet intrinsically low in sodium chloride (approximately 10 mmoles NaCl/70 kg body weight/day). A sodium chloride supplement is added in an amount sufficient to increase total sodium intake to 140 meq/day/70 kg. The diet provides approximately 55 mmoles of potassium, 375 mg of calcium, and 820 mg of phosphorus per 70 kg/day.

In each patient, the total number of calories provided is determined from the estimated amount of energy required to keep body weight constant. The diet contains, as a percentage of total calories, 35% fat, 56% carbohydrate, and 9% protein. The specific ingredients of each meal are kept constant throughout the study. Fluid intake would be fixed at 3150 ml/70 kg/day.

A 10-day steady state control period precedes the experimental period for all subjects. Throughout the experimental period, all patients in the treatment group initially receive pulsed stimulation of selected sympathetic nerves using an implanted neurostimulation device with pulse duration of from about 1 to about 10800 seconds at a frequency no less than about 1 to about 1440 per day. Control subjects would have similar devices implanted but would not receive pulsed stimulation for the duration of the treatment period.

Blood pressure is measured in the nondominant arm at 8 am, noon, 4 pm, 8 pm, and 10 pm of each day, with an automated oscillometric device (Dinamap) in order to avoid observer bias. At each measurement session, after the patient has been supine for 10 minutes, five measurements of systolic and diastolic pressure and heart rate are obtained and the average of the last four measurements are calculated. The measurements are repeated with the patient in the upright position at each session. The measurements are averaged to yield values for daily systolic and diastolic blood pressures. Mean arterial pressure is calculated as (systolic pressure–diastolic pressure)/3+diastolic pressure. Measurements continue for a recovery period of 15 days following completion of pulsed administration.

In accordance with changes in the measured parameters, the schedule of administration of pulses would be actively modified in the following manner: for any increase in systolic pressure of greater than 1-10 mm Hg or diastolic pressure of greater than 1-10 mm Hg, the frequency of administration of pulses is decreased by 1-1440 per day and/or the duration of each pulse is decreased by 1-10800 seconds. For any decrease in systolic pressure of greater than 1-10 mm Hg or diastolic pressure of greater than 1-10 mm Hg, the frequency of administration of pulses is increased by 1-1440 per day and/or the duration of each pulse is increased by 1-10800 seconds.

In order to assess potential effects in other systems where sympathetic activity typically exerts influence, the following parameters may be assessed with the accompanying range of values observed as indicated:

|  | Test | Reference value | Claimed Range |
|---|---|---|---|
| pulmonary gas | Alveolar oxygen | 650-713 mmHg | 600-713 mmHg |
| serum blood gas | pH | 7.35-7.45 | 7.1 to 7.7 |
|  | arterial pO2 | 80-100 mmHg | 50-110 |
|  | arterial pCO2 | 35-45 mmHg | 10 to 80 |
|  | arterial bicarb | 25-35 meq/L | 10 to 40 |
|  | alveolar/oxygen ratio | 0.8 | 1 to 0.6 |
|  | aa gradient | 10-15 mmHg | 5 to 120 |
|  | venous oxygen sat | 60% | 30-80% |
| cardoipulmonary | cardiac output | 3.5 to 5.5 L/min | 1 to 6 |
|  | cardiac index | 2.8-3.2 L/min/m2 | 0.5 to 6 |
|  | right atrial pressure | 1-7 mmHg | 1 to 30 |
|  | right ventricular systolic pressure | 15-25 mmHg | 5 to 50 |
|  | right ventricular diastolic pressure | 0-8 mm Hg | 1 to 50 |
|  | pulmonary arterial systolic pressure | 15-25 mmHg | 5 to 50 |
|  | pulmonary arterial diastolic pressure | 8-15 mmHg | 1 to 30 |
|  | mean pulmonary arterial pressure | 10-20 mmHg | 5 to 50 |
|  | pulmonary capillary wedge pressure | 6-12 mmHg | 1 to 20 |
| pulmonary function test | tidal volume | 8-15 ml/Kg | 2-20 or 20-80% |
|  | total lung capacity | 5-7 liters | 3 to 10 or 20-120% |
|  | residual volume | 1.5 to 2.5 liters | 0.5 5 or 20-120% |
|  | forced expiratory volume in 1 second | 3.5-4 liters | 0.5 to 6 or 20-120% |
|  | functional vital capacity | 4-6 liters | 0.5 to 6 or 20-120% |
|  | FEV1/FVC ratio | >75% | 20-120% |
|  | forced expiratory flow | 75-125% | 50 to 150% |
|  | peak expiratory flow rate | 80-100% | 60-120% |

-continued

| | Test | Reference value | Claimed Range |
|---|---|---|---|
| | forced expiratory time | <5 seconds | 0-20 seconds |
| | corrected diffusion capacity | 75-80% | 60-140% |
| | corrected QT interval | <440 | <600 |
| sleep study | sleep latency | >10 min | 0-1 hour |
| | total sleep time | >5.5 hours | 0-12 hours |
| | percent rem | >15% of TST | 0-40% total sleep time |
| | percent stage 3-4 non rem | >25% of TST | 0-50% total sleep time |
| | respiratory arousal index | <5/hour total sleep time | 0-40/hour total sleep time |
| | periodic leg movements | <1/hour total sleep time | 0-40/hour total sleep time |
| | apnea index | <1/hour total sleep time | 0-20/hour total sleep time |
| | hypopnea index | <3/hour total sleep time | 0-40/hour total sleep time |
| | nadir oxygen saturatin | >92% | 40-100% |
| | mean oxygen saturation | >95% | 40-100% |
| | desaturation index | <5 defined as >4% for 5 seconds/hour of total sleep time | 0-40 defined as >4% for 5 seconds/hour of total sleep time |
| | highest carbon dioxide | 52 mmHg | 10-80 mmHg |
| | carbon dioxide >45 mmHg | <20% of total sleep time | 0-60% of total sleep time |
| Serum Markers | Catecholamine levels | | |
| | Acetycholine levels | 650-1500 IU/L | 300-2000 IU/L |
| | Aldosterone levels | 17-70 nmol/day | 5-150 nmol/L/day |
| | Renin levels | 7-76 uU/mL | 3-200 uU/ml |
| | Vasopressin levels | 2-8 pg/mL | 1-20 pg/ml |
| | angiotensin converting enzyme levels | 25-100 IU/L | 5-200 U/L |
| | interleukin 1-3 and 5-13 and 18 | modulate | |
| | Interleukin 4 | decrease | |
| | interferon alpha and beta | modulate | |
| | interferon gamma | increase | |
| | tumor necrosis factor alpha | modulate | |
| | transforming growth factor | modulate | |
| | hemoglobin A1C | 4-8% | 2-12% |
| | Fasting glucose | 3.5-6.0 mmol/L | 1-10 mmol/L |
| | high density lipoprotein | 45-60 | 10 to 90 |
| | low density lipoprotein | 95-130 | 60-200 |
| | triglyceride | <2 mmol/L | 4 to 4 mmol/L |
| | beta natriuretic peptide | 20-40 pg/mL | 0-100 pg/mL |
| | alpha natriuretic peptide | 20-40 pg/mL | 0-50 pg/mL |
| | erythrocyte sedimentation rate | 0-35 mm/Hour | 1-200 mm/Hour |
| | c reactive peptide | <10 mg/L | 1-80 mg/L |
| | transferrin | 1.75 to 3.13 g/L | 0.5 to 6 g/L |
| | Hemloglobin | 135-160 gm/L | 25 to 300 gm/L |
| | hematocrit | 37-54% | 25-60% |
| | ferritin | 20-240 ug/L | 5 to 600 ug/L |
| | iron | 10-40 umol/L | 5 to 100 umol/L |
| | cholinesterase | 650-1500 IU/L | 200-2500 IU/L |
| | Urine adrenaline | 0-80 nmol/day | 0-200 nmol/day |
| | Urine noradrenaline | 0-780 nmol/day | 0-1600 nmol/day |
| | Urine dopamine | 0-3500 nmol/day | 0-7000 nmol/day |
| | adrenocorticotrophic hormone | <19 pmol/L | 0 to 40 pmol/L |
| | antidiuretic hormone | 2-8 pg/mL | 1-20 pg/mL |
| | thrombin clotting | 10-20 secs | 5-30 secs |

| | Test | Reference value | Claimed Range |
|---|---|---|---|
| | time | | |
| | total serum cholesterole | 110-120 | 100-300 |
| Additional | body mass index | 20-30 | <40 |
| | systolic blood pressure | <125 | 90-180 |
| | diastolic blood pressure | <75 | 30-100 |
| | pulse pressure | <20 | 20-40 |
| | heart rate | 60-100 | 30-200 |
| | heart rate variability | increase | |
| | respiratory sinus arrhythmia | increase | |

All patients in the treatment group initially have either no changes or statistically negligible increases in systolic, diastolic, and mean arterial pressures while the compensatory response to administration begins to take hold. At some point during the experimental period these patients begin to manifest reductions in systolic, diastolic, and mean arterial pressures. The frequency and duration of pulses is gradually increased so as to increase the magnitude of the reduction for the duration of the experimental period. These reductions are maintained upon cessation of the treatment for the duration of the recovery period. Patients in the control group maintain the same values in these parameters throughout both the control period and the experimental period. No adverse effects of treatment are found in any of these subjects.

Example Study 2

Effect of Paradoxical Pulsed Neurostimulation Therapy in Normotensive Patients

In double blinded randomized controlled studies performed in similar fashion to that described in Example 1, the effect of intermittent stimulation of sympathetic nerves on the blood pressure in normotensive individuals is determined. The control period in this case is again 10 days and the experimental period 30 days. Again, patients in the treatment group receive pulsed stimulation of selected sympathetic nerves using an implanted neurostimulation device with pulse duration 1-10800 seconds at a frequency no less than 1-1440 per day. The schedule of pulse administration is adjusted during the course of the experimental period by the protocol as previously noted. Control subjects have similar devices implanted but do not receive any pulsed stimulation for the duration of the treatment period. The subjects are fed a diet having an intrinsic low-sodium chloride content (less than 10 meq sodium and chloride/day/70 kg body weight) and a normal potassium content (52 meq/day/70 kg body weight). A sodium chloride supplement is added sufficient to increase total sodium intake to 140 meq/70 kg/day.

As with the hypertensive individuals, pulsed electrical stimulation of sympathetic nerves results in significant reductions in mean arterial pressures maintained upon cessation of treatment. Patients in the control group maintain the same mean arterial pressure throughout both the control period and the experimental period. Findings of reduction in normotensive individuals means that paradoxical pulsed therapy finds prophylactic use in preventing the onset of hypertension in individuals identified as predisposed to the condition.

Materials and Methods

1. Method for Stimulation of Sympathetic Activity

Splanchnic nerves are ideal candidates for sympathetic nerve stimulation given their size and location. An electrical device for stimulation is adapted for application to relevant nerve bundles. The electrodes of this device consist of bipolar electrodes that generate action potentials by cathodic stimulation and produce a complete anodal block on one side of the cathode to make the electrode-generated action potentials unidirectional. Each bipolar electrode contains an insulating base with cathode and anode on one face and control circuitry on the opposite face. This apparatus communicates with a master control unit either attached to the bipolar electrodes directly via an asynchronous serial bus or via wireless communication link. 1-5 Hz has been described as the frequency that best describes the conduction velocity, latency, and refractory period of sympathetic nerves, and range of amplitude of current delivered can vary between 0.1 and 20 A.

2. Method for Inhibition of Parasympathetic Activity

Alternatively, the vagus nerve offers a candidate for increasing relative sympathetic activity via inhibition of parasympathetic activity. An electrical device for stimulation is adapted for application to relevant nerve bundles. The electrodes for this device consist of tripolar electrodes that produce a complete block of vagal activity by generating action potentials via cathodic stimulation and imposing complete anodal blocks in either direction. Each tripolar electrode contains an insulating base with cathodes and anodes on one face and control circuitry on the opposite face. This apparatus communicates with a master control unity either attached to the tripolar electrodes directly via an asynchronous serial bus or via wireless communication link. 10-150 Hz has been described as the frequency that best describes the conduction velocity, latency, and refractory period of parasympathetic nerves, and range of amplitude of current delivered can vary between 0.1 and 20 A.

II. Example of Paradoxical Pulsed Therapy Using Pharmacologic Stimulation

An example of utilizing pulsed paradoxical therapy for the treatment of hypertension includes using a short-acting sympathomimetic agent to produce short intervals of increased blood pressure ranging from seconds to hours to increase dynamic range. Alternatively, or in addition, one could deploy a short-acting parasympathomimetics agent to induce to induce short intervals of decreased blood pressure ranging from seconds to hours to increase dynamic range. In addition, one could use measured feedback to regulate the frequency and duration of pulsed therapies.

A. Dog Studies

Example Study 1:

Effect of Paradoxical Pulsed Pharmacologic Therapy in Hypertensive Dogs

Double-blinded randomized controlled studies are performed in a set of dogs with experimentally induced hypertension (mechanism of induction to be determined) to demonstrate that intermittent stimulation with sympathomimetic pharmacologic agents lowers blood pressure. Experiments are conducted on mongrel dogs of either sex weighing 14-17 kg. Dogs are prepared for study by being treated for ectoparasites and endoparasites in addition to being immunized for parvovirus, canine distemper, hepatitis, parainfluenza, and coronavirus. All experiments are conducted in accordance with the National Institutes of Health Guide for the Care and Use of Laboratory Animals. Dogs are fed a low sodium diet supplemented with sodium chloride to achieve a sodium intake of 40 mmol/d (normal sodium intake). This dietary regimen provides a constant and known level of dietary sodium intake. Throughout the experimental protocol, all dogs are allowed water ad libitum.

For implantation of catheters for controlled administration of the agents, dogs are anesthetized with sodium thiamylal (30 mg/kg IV) for induction and then halothane (1%). Catheters are inserted via the femoral vessels into the aorta for direct arterial pressure measurement and drug administration. All catheter lines are tunneled subcutaneously to the midscapular region of the back and exteriorized. A 10-day steady state control period precedes the experimental period for all subjects to allow for recovery from surgical instrumentation.

Throughout the experimental period, dogs in the treatment group initially receive pulsed stimulation via pulsatile administration of a sympathomimetic agent at a frequency no less than 1 to about 1440 pulses per day. Dogs in the control group receive a placebo at the same frequency during the experimental period. Measurement of systolic, diastolic, and mean arterial blood pressures are obtained via pressure transducer on an ongoing basis. Measurements continue for a recovery period of 15 days following completion of pulsed administration.

In accordance with changes in the measured parameters, the schedule of administration of pulses is actively modified in the following manner: for any increase in systolic pressure of greater than 1-10 mm Hg or diastolic pressure of greater than 1-10 mm Hg, the frequency of administration of the agent is decreased by 1-1440 per day and/or the dosing of the agent is decreased by 1-99%. For any decrease in systolic pressure of greater than 1-10 mm Hg or diastolic pressure of greater than 1-10 mm Hg, the frequency of administration of the agent is increased by 1-1440 per day and/or the dosing of the agent is increased by 1-99%.

In order to assess potential effects in other systems where sympathetic activity typically exerts influence, arterial blood samples and pulmonary function tests are obtained on a weekly schedule where the following parameters may be assessed:

| Test | |
|---|---|
| pulmonary gas | Alveolar oxygen |
| serum blood gas | pH |
| | arterial pO2 |
| | arterial pcO2 |
| | arterial bicarb |
| | alveolar/oxygen ratio |
| | aa gradient |
| | venous oxygen sat |
| cardoipulmonary | cardiac output |
| | cardiac index |
| | right atrial pressure |
| | right ventricular systolic pressure |
| | right ventricular diastolic pressure |
| | pulmonary arterial systolic pressure |
| | pulmonary arterial diastolic pressure |
| | mean pulmonary arterial pressure |
| | pulmonary capillary wedge pressure |
| pulmonary function test | tidal volume |
| | total lung capacity |
| | residual volume |
| | forced expiratory volume in 1 second |
| | functional vital capacity |
| | FEV1/FVC ratio |
| | forced expiratory flow |
| | peak expiratory flow rate |
| | forced expiratory time |
| | corrected diffusion capacity |
| | corrected QT interval |
| sleep study | sleep latency |
| | total sleep time |
| | percent rem |
| | percent stage 3-4 non rem |
| | respiratory arousal index |
| | periodic leg movements |
| | apnea index |
| | hypopnea index |
| | nadir oxygen saturatin |
| | mean oxygen saturation |
| | desaturation index |
| | highest carbon dioxide |
| | carbon dioxide >45 mmHg |
| Serum Markers | Catecholamine levels |
| | Acetycholine levels |
| | Aldosterone levels |
| | Renin levels |
| | Vasopressin levels |
| | angiotensin converting enzyme levels |
| | interleukin 1-3 and 5-13 and 18 |
| | Interleukin 4 |
| | interferon alpha and beta |
| | interferon gamma |
| | tumor necrosis factor alpha |
| | transforming growth factor |
| | hemoglobin A1C |
| | Fasting glucose |
| | high density lipoprotein |
| | low density lipoprotein |
| | triglyceride |
| | beta natriuretic peptide |
| | alpha natriuretic peptide |
| | erythrocyte sedimentation rate |
| | c reactive peptide |
| | transferrin |
| | Hemloglobin |
| | hematocrit |
| | ferritin |
| | iron |
| | cholinesterase |
| | Urine adrenaline |
| | Urine noradrenaline |
| | Urine dopamine |
| | adrenocorticotrophic hormone |
| | antidiuretic hormone |
| | thrombin clotting time |
| | total serum cholesterole |
| Additional | body mass index |
| | systolic blood pressure |
| | diastolic blood pressure |
| | pulse pressure |
| | heart rate |
| | heart rate variability |
| | respiratory sinus arrhythmia |

All dogs in the treatment group are observed to initially have either no changes or statistically negligible increases in systolic, diastolic, and mean arterial pressures while the compensatory response to administration began to take hold. At some point during the experimental period these dogs are observed to begin to manifest reductions in systolic, diastolic, and mean arterial pressures. The frequency and dosage of administration is gradually adjusted so as to increase the magnitude of the reduction for the duration of the experimental period. These reductions are maintained upon cessation of the treatment for the duration of the recovery period. Dogs in the control group maintain the same values in these parameters throughout both the control period and the experimental period. No adverse effects of treatment are found in any of these subjects.

Example Study 2:

Effect of Paradoxical Pulsed Pharmacologic Therapy in Normotensive Dogs

In double-blinded randomized controlled studies performed in similar fashion to that described in Example 1, the effect of pulsed stimulation via pulsatile administration of sympathomimetic agents on the blood pressure in normotensive dogs is determined. The control period in this case is 10 days and the experimental period 30 days. Again, dogs in the treatment group receive pulsed stimulation via pulsatile administration of a sympathomimetic agent at a frequency no less than about 1 to about 1440 per day. The schedule of pulse administration is adjusted during the course of the experimental period by the protocol as previously noted. Control subjects have comparable devices for administration but receive a placebo for the duration of the treatment period.

As with the hypertensive dogs, the pulsatile administration of a sympathomimetic agent in normotensive dogs results in significant reductions in mean arterial pressures maintained upon cessation of treatment. Dogs in the control group maintain the same mean arterial pressure throughout both the control period and the experimental period. Findings of reduction in normotensive dogs show that paradoxical pulsed therapy readily finds prophylactic use in preventing the onset of hypertension in individuals identified as predisposed to the condition.

B. Human Studies

Example Study 1:

Effect of Paradoxical Pulsed Pharmacologic Therapy in Hypertensive Patients

Double-blinded randomized controlled studies are performed in a set of patients with essential hypertension to demonstrate that intermittent electrical stimulation of sympathetic nerves lowers blood pressure. In all patients, hypertension is confirmed on at least three occasions in an outpatient setting after the patient has been sitting for at least 10 minutes. Blood pressure ranges recorded indicate elevation of both systolic and diastolic components of the blood pressure. No patients have clinical signs or symptoms of pheochromocytoma or renal artery stenosis, and no patients have clinical or laboratory evidence of impaired cardiac, renal, pulmonary, or hepatic function. Urinalysis and serum concentrations of creatinine, sodium, and potassium are confirmed to be within normal limits for patients.

All medications are stopped for each individual for at least four weeks before the beginning of the study. All patients remain hospitalized throughout the study, where physical activity consists of only daily walks. Throughout the study, each patient ingests a constant amount of a nutritionally adequate whole-foods diet intrinsically low in sodium chloride (approximately 10 mmoles NaCl/70 kg body weight/day). A sodium chloride supplement is added in an amount sufficient to increase total sodium intake to 140 meq/day/70 kg. The diet provides approximately 55 mmoles of potassium, 375 mg of calcium, and 820 mg of phosphorus per 70 kg/day.

In each patient, the total number of calories provided is determined from the estimated amount of energy required to keep body weight constant. The diet contains, as a percentage of total calories, 35% fat, 56% carbohydrate, and 9% protein. The specific ingredients of each meal are kept constant throughout the study. Fluid intake would be fixed at 3150 ml/70 kg/day.

A 10-day steady state control period precedes the experimental period for all subjects. Throughout the experimental period, all patients in the treatment group initially receive pulsatile administration of a sympathomimetic agent via an implanted intravenous catheter at a frequency no less than about 1 to about 1440 per day. Control subjects would have similar catheters implanted but would receive only placebo for the duration of the treatment period.

Blood pressure is measured in the nondominant arm at 8 am, noon, 4 pm, 8 pm, and 10 pm of each day, with an automated oscillometric device (Dinamap) in order to avoid observer bias. At each measurement session, after the patient has been supine for 10 minutes, five measurements of systolic and diastolic pressure and heart rate are obtained and the average of the last four measurements are calculated. The measurements are repeated with the patient in the upright position at each session. The measurements are averaged to yield values for daily systolic and diastolic blood pressures. Mean arterial pressure is calculated as (systolic pressure–diastolic pressure)/3+diastolic pressure. Measurements continue for a recovery period of 15 days following completion of pulsed administration.

In accordance with changes in the measured parameters, the schedule of administration of pulses would be actively modified in the following manner: for any increase in systolic pressure of greater than 1-10 mm Hg or diastolic pressure of greater than 1-10 mm Hg, the frequency of administration is decreased by 1-1440 per day and/or the dosing of the agent is decreased by 1-99%. For any decrease in systolic pressure of greater than 1-10 mm Hg or diastolic pressure of greater than 1-10 mm Hg, the frequency of administration is increased by 1-1440 per day and/or the dosing of the agent is increased by 1-99%.

In order to assess potential effects in other systems where sympathetic activity typically exerts influence, the following parameters may be assessed with the accompanying range of values observed as indicated:

|  | Test | Reference value | Claimed Range |
|---|---|---|---|
| pulmonary gas | Alveolar oxygen | 650-713 mmHg | 600-713 mmHg |
| serum blood gas | pH | 7.35-7.45 | 7.1 to 7.7 |
|  | arterial pO2 | 80-100 mmHg | 50-110 |
|  | arterial pCO2 | 35-45 mmHg | 10 to 80 |
|  | arterial bicarb | 25-35 meq/L | 10 to 40 |
|  | alveolar/oxygen ratio | 0.8 | 1 to 0.6 |
|  | aa gradient | 10-15 mmHg | 5 to 120 |
|  | venous oxygen sat | 60% | 30-80% |

-continued

|  | Test | Reference value | Claimed Range |
|---|---|---|---|
| cardoipulmonary | cardiac output | 3.5 to 5.5 L/min | 1 to 6 |
|  | cardiac index | 2.8-3.2 L/min/m2 | 0.5 to 6 |
|  | right atrial pressure | 1-7 mmHg | 1 to 30 |
|  | right ventricular systolic pressure | 15-25 mmHg | 5 to 50 |
|  | right ventricular diastolic pressure | 0-8 mm Hg | 1 to 50 |
|  | pulmonary arterial systolic pressure | 15-25 mmHg | 5 to 50 |
|  | pulmonary arterial diastolic pressure | 8-15 mmHg | 1 to 30 |
|  | mean pulmonary arterial pressure | 10-20 mmHg | 5 to 50 |
|  | pulmonary capillary wedge pressure | 6-12 mmHg | 1 to 20 |
| pulmonary function test | tidal volume | 8-15 ml/Kg | 2-20 or 20-80% |
|  | total lung capacity | 5-7 liters | 3 to 10 or 20-120% |
|  | residual volume | 1.5 to 2.5 liters | 0.5 5 or 20-120% |
|  | forced expiratory volume in 1 second | 3.5-4 liters | 0.5 to 6 or 20-120% |
|  | functional vital capacity | 4-6 liters | 0.5 to 6 or 20-120% |
|  | FEV1/FVC ratio | >75% | 20-120% |
|  | forced expiratory flow | 75-125% | 50 to 150% |
|  | peak expiratory flow rate | 80-100% | 60-120% |
|  | forced expiratory time | <5 seconds | 0-20 seconds |
|  | corrected diffusion capacity | 75-80% | 60-140% |
|  | corrected QT interval | <440 | <600 |
| sleep study | sleep latency | >10 min | 0-1 hour |
|  | total sleep time | >5.5 hours | 0-12 hours |
|  | percent rem | >15% of TST | 0-40% total sleep time |
|  | percent stage 3-4 non rem | >25% of TST | 0-50% total sleep time |
|  | respiratory arousal index | <5/hour total sleep time | 0-40/hour total sleep time |
|  | periodic leg movements | <1/hour total sleep time | 0-40/hour total sleep time |
|  | apnea index | <1/hour total sleep time | 0-20/hour total sleep time |
|  | hypopnea index | <3/hour total sleep time | 0-40/hour total sleep time |
|  | nadir oxygen saturatin | >92% | 40-100% |
|  | mean oxygen saturation | >95% | 40-100% |
|  | desaturation index | <5 defined as >4% for 5 seconds/hour of total sleep time | 0-40 defined as >4% for 5 seconds/hour of total sleep time |
|  | highest carbon dioxide | 52 mm Hg | 10-80 mmHg |
|  | carbon dioxide >45 mmHg | <20% of total sleep time | 0-60% of total sleep time |
| Serum Markers | Catecholamine levels |  |  |
|  | Acetycholine levels | 650-1500 IU/L | 300-2000 IU/L |
|  | Aldosterone levels | 17-70 nmol/day | 5-150 nmol/L/day |
|  | Renin levels | 7-76 uU/mL | 3-200 uU/ml |
|  | Vasopressin levels | 2-8 pg/mL | 1-20 pg/ml |
|  | angiotensin converting enzyme levels | 25-100 IU/L | 5-200U/L |
|  | interleukin 1-3 and 5-13 and 18 | modulate |  |
|  | Interleukin 4 | decrease |  |
|  | interferon alpha and beta | modulate |  |
|  | interferon gamma | increase |  |
|  | tumor necrosis factor alpha | modulate |  |
|  | transforming growth factor | modulate |  |
|  | hemoglobin A1C | 4-8% | 2-12% |
|  | Fasting glucose | 3.5-6.0 mmol/L | 1-10 mmol/L |

-continued

| | Test | Reference value | Claimed Range |
|---|---|---|---|
| | high density lipoprotein | 45-60 | 10 to 90 |
| | low density lipoprotein | 95-130 | 60-200 |
| | triglyceride | <2 mmol/L | 4 to 4 mmol/L |
| | beta natriuretic peptide | 20-40 pg/mL | 0-100 pg/mL |
| | alpha natriuretic peptide | 20-40 pg/mL | 0-50 pg/mL |
| | erythrocyte sedimentation rate | 0-35 mm/Hour | 1-200 mm/Hour |
| | c reactive peptide | <10 mg/L | 1-80 mg/L |
| | transferrin | 1.75 to 3.13 g/L | 0.5 to 6 g/L |
| | Hemloglobin | 135-160 gm/L | 25 to 300 gm/L |
| | hematocrit | 37-54% | 25-60% |
| | ferritin | 20-240 ug/L | 5 to 600 ug/L |
| | iron | 10-40 umol/L | 5 to 100 umol/L |
| | cholinesterase | 650-1500 IU/L | 200-2500 IU/L |
| | Urine adrenaline | 0-80 nmol/day | 0-200 nmol/day |
| | Urine noradrenaline | 0-780 nmol/day | 0-1600 nmol/day |
| | Urine dopamine | 0-3500 nmol/day | 0-7000 nmol/day |
| | adrenocorticotrophic hormone | <19 pmol/L | 0 to 40 pmol/L |
| | antidiuretic hormone | 2-8 pg/mL | 1-20 pg/mL |
| | thrombin clotting time | 10-20 secs | 5-30 secs |
| | total serum cholesterole | 110-120 | 100-300 |
| Additional | body mass index | 20-30 | <40 |
| | systolic blood pressure | <125 | 90-180 |
| | diastolic blood pressure | <75 | 30-100 |
| | pulse pressure | <20 | 20-40 |
| | heart rate | 60-100 | 30-200 |
| | heart rate variability | increase | |
| | respiratory sinus arrhythmia | increase | |

All patients in the treatment group initially have either no changes or statistically negligible increases in systolic, diastolic, and mean arterial pressures while the compensatory response to administration begins to take hold. At some point during the experimental period these patients begin to manifest reductions in systolic, diastolic, and mean arterial pressures. The frequency and dosage of administration is gradually adjusted so as to increase the magnitude of the reduction for the duration of the experimental period. These reductions are maintained upon cessation of the treatment for the duration of the recovery period. Patients in the control group maintain the same values in these parameters throughout both the control period and the experimental period. No adverse effects of treatment are found in any of these subjects.

Example Study 2

Effect of Paradoxical Pulsed Pharmacologic Therapy in Normotensive Patients

In double blinded randomized controlled studies performed in similar fashion to that described in Example 1, the effect of intermittent stimulation of sympathetic nerves on the blood pressure in normotensive individuals is determined. The control period in this case is again 10 days and the experimental period 30 days. Again, patients in the treatment group receive pulsatile administration of a sympathomimetic agent via implanted intravenous catheter at a frequency no less than 1-1440 per day. The schedule of pulse administration is adjusted during the course of the experimental period by the protocol as previously noted. Control subjects have similar catheters implanted but receive only placebo for the duration of the treatment period. The subjects are fed a diet having an intrinsic low-sodium chloride content (less than 10 meq sodium and chloride/day/70 kg body weight) and a normal potassium content (52 meq/day/70 kg body weight). A sodium chloride supplement is added sufficient to increase total sodium intake to 140 meq/70 kg/day.

As with the hypertensive individuals, pulsatile administration of a sympathomimetic agent results in significant reductions in mean arterial pressures maintained upon cessation of treatment. Patients in the control group maintain the same mean arterial pressure throughout both the control period and the experimental period. Findings of reduction in normotensive individuals means that paradoxical pulsed therapy finds prophylactic use in preventing the onset of hypertension in individuals identified as predisposed to the condition Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject for hypertension, said method comprising
enhancing at least one symptom of hypertension by applying electrical stimulus to sympathetic nerves of said subject;
removing said stimulus to provide a holiday period which permits said subject to mount a compensatory response characterized by a decrease in said symptom;
monitoring said compensatory response; and
repeating said enhancing, removing, and monitoring in a manner effective to treat hypertension,
wherein said stimulus is applied in a irregularly irregular manner and the duration of holiday periods varies randomly over the entire course of a treatment.

2. The method according to claim 1, wherein the holiday period is 1 day or longer.

3. The method according to claim 2, wherein the holiday period is 5 days or longer.

4. The method according to claim 1, wherein the stimulus is applied for one week or less.

5. The method according to claim 1, wherein the stimulus is applied for 3 days or less.

6. The method according to claim 1, wherein the stimulus is applied for 1 day or less.

7. The method according to claim 1, wherein the applying is pulsatile.

8. The method according to claim 1, wherein the symptom is enhanced two-fold or more.

* * * * *